(12) United States Patent
Barere

(10) Patent No.: US 7,575,570 B2
(45) Date of Patent: *Aug. 18, 2009

(54) SYRINGE ASSEMBLY HAVING DISABLING MECHANISM

(75) Inventor: Aaron Barere, Hoboken, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/019,795

(22) Filed: Jan. 25, 2008

(65) Prior Publication Data

US 2008/0215000 A1 Sep. 4, 2008

Related U.S. Application Data

(63) Continuation of application No. 11/063,455, filed on Feb. 23, 2005, now Pat. No. 7,331,935.

(60) Provisional application No. 60/638,089, filed on Dec. 21, 2004.

(51) Int. Cl.
*A61M 5/00* (2006.01)

(52) U.S. Cl. ....................................... 604/110

(58) Field of Classification Search ................. 604/110, 604/181, 187, 192–198, 207–210, 218–229, 604/241
See application file for complete search history.

(56) References Cited

U.S. PATENT DOCUMENTS

| 5,738,655 | A  | * | 4/1998 | Vallelunga et al. | 604/110 |
| 7,331,934 | B2 | * | 2/2008 | Suresh et al.     | 604/110 |
| 7,331,935 | B2 | * | 2/2008 | Barere            | 604/110 |
| 7,399,293 | B2 | * | 7/2008 | Oyibo et al.      | 604/110 |
| 7,407,495 | B2 | * | 8/2008 | Barere et al.     | 604/228 |

* cited by examiner

*Primary Examiner*—Matthew F DeSanto
(74) *Attorney, Agent, or Firm*—Jeanne P. Lukasavage

(57) ABSTRACT

A syringe assembly having passive disabling structure includes a barrel and a plunger rod assembly. The plunger rod assembly includes a plunger rod and a stopper connected by an indexing locking element. The number of strokes of the syringe plunger before the stopper is locked into the barrel rendering the syringe assembly unusable is determined by the number of detents on the plunger rod and stopper which engage the locking mechanism. Upon completion of the final delivery stroke, any attempt to withdraw the plunger rod from the barrel will cause the locking element to engage the barrel and trap the stopper in the barrel preventing further use of the syringe.

29 Claims, 20 Drawing Sheets

SYRINGE ASSEMBLY HAVING DISABLING MECHANISM

This application is a continuation of U.S. application Ser. No. 11/063,455, filed on Feb. 23, 2005, which claims priority to Provisional Application No. 60/638,089, filed Dec. 21, 2004, now abandoned.

BACKGROUND OF THE INVENTION

The present invention relates to syringe assemblies and particularly to syringe assemblies having an automatic disabling mechanism.

Throughout the world the multiple use of hypodermic syringe products which are intended for single-use only, is instrumental in drug abuse and in the transfer of contagious diseases. Intravenous drug users who routinely share and re-use syringes are a high-risk group with respect to the AIDS virus. Also, the effects of multiple use are a major concern in some countries where repeated use of syringe products during mass immunization programs may be responsible for the spread of many diseases. Re-use of single-use hypodermic syringe assemblies is also instrumental in the spread of drug abuse even in the absence of infection or disease.

Many attempts have been made to remedy this problem. Most notable are early contributions which relied on a specific act to destroy the syringe after use either by using a destructive device or providing a syringe assembly with frangible zones so that the syringe could be rendered inoperable by the application of force. Other attempts involve the inclusion of structure which would allow the destruction or defeating of the syringe function to a conscious act by the syringe user. Although many of these devices work quite well, they do require the specific intent of the user followed by the actual act to destroy or render the syringe inoperable. These devices are not effective with a user having the specific intent to re-use the hypodermic syringe. Accordingly, there was a need for a single-use hypodermic syringe which after use will become inoperable or incapable of further use automatically without any additional act on the part of the user. The automatic function is much harder to provide because the means for rendering the syringe inoperable must not prevent its filling or use under normal conditions.

A single-use syringe which automatically disables after injection is taught in U.S. Pat. No. 4,973,310 to Kosinski. This syringe contains a locking element positioned in the syringe barrel between the plunger rod and the inside surface of the barrel. In use, the syringe allows the user to draw a pre-selected amount of medication into the chamber of the barrel and deliver this medication, as through injection, into the patient. Any attempt to withdraw the plunger to use the syringe a second time will cause the locking element to embed itself into the inside surface of the syringe barrel to prevent proximal motion of the plunger rod.

There is still a need for a single-use syringe which will allow a pre-selected number of plunger rod strokes before the automatic disabling mechanism activates. For example, four strokes of the plunger may be required to complete the injection process, such as when the syringe assembly is used to draw a diluent into the syringe barrel, dispense the diluent into a vial containing the substance to be reconstituted, drawing back the reconstituted medication into the syringe and then delivering the contents of the syringe into the patient.

SUMMARY OF THE INVENTION

The present invention is directed to a syringe assembly having a passive disabling mechanism. The disabling mechanism enables variable dosages by the syringe assembly and enables a selected number of cycles or strokes by the plunger rod before being disabled. In one preferred embodiment, the disabling mechanism provides two aspirating and two dispensing cycles before being disabled. The assembly enables the aspiration and dispensing of a selected volume of a diluent into a vial to reconstitute a drug, pharmaceutical agent, or other substance and then aspirating the reconstituted substance back into the syringe. A selected volume of the reconstituted substance can be injected or delivered to a patient where the volume of the substance that is delivered can be the same or different than the volume of the substance aspirated into the syringe barrel. The syringe is automatically disabled after the injection or delivery stroke by retracting the plunger rod.

The disabling mechanism is actuated by the axial movement of the plunger rod with respect to the syringe barrel and to the stopper, by moving the plunger rod in the aspirating direction. The stopper is coupled to the plunger rod through structure that allows limited axial movement of the stopper with respect to the plunger rod. The disabling mechanism is moved through a series of stages by reversing the direction of the axial movement of the plunger rod with respect to the stopper to move the mechanism in a step-wise manner to the disabling position. The disabling position of the mechanism is attained by the relative movement between the plunger rod and the stopper and is not dependent on the position of the stopper within the syringe barrel or the length of the stroke by the stopper. In this manner, the syringe assembly is able to dispense a desired volume of the drug or other substance, and the disabling mechanism can be actuated after the final dispensing or injection stroke regardless of the position of the stopper in the syringe barrel. By actuating the disabling mechanism, the stopper cannot be retracted to aspirate another dose into the syringe barrel but allows any substance remaining in the syringe barrel to be dispensed.

The present syringe assembly provides an improvement over prior art devices by allowing a variable dose of diluent, chosen by the user at the time of use, to be drawn into the syringe, dispensing the diluent into a vial containing a substance to be reconstituted, drawing a selected amount of the reconstituted substance back into the syringe and then delivering the contents of the syringe. The selected amount of the reconstituted substance may be equal or less than the full volume reconstituted at the discretion of the user. The syringe assembly is automatically disabled after the final injection stroke by reversing the direction of the movement of the plunger rod from the dispensing direction to the aspirating direction. After the injection stroke of the syringe plunger, the plunger rod is retracted to activate the disabling mechanism to prevent axial movement of the stopper toward the proximal end of the syringe barrel thereby preventing the stopper from being removed and preventing reuse of the syringe to draw fluid into its chamber.

When the present syringe assembly has two or more detents on the stopper and one or more detents in the plunger rod, the maximum number of strokes the syringe assembly will allow can be varied by the initial position of the locking element with respect to the stopper detents and the plunger rod detents.

The present syringe assembly provides an improvement over prior art devices by providing a structure wherein the elements which allow the lost motion between the plunger rod and the stopper are contained internally within the plunger rod, safe from attempts to deflect the syringe barrel and plunger to defeat the locking mechanism. If these elements were on the outside of the plunger rod, it may be possible to deflect the barrel to contact the elements and defeat the locking mechanism.

Another important advantage of the present invention is that in many embodiments, detents and discontinuities that function to achieve the desired result are annular, so that rotating the plunger rod with respect to the barrel will not distort, damage or defeat the locking element. A single use syringe will not be effective if it can be easily manipulated to overcome the locking mechanism for removing the components for re-assembly and reuse.

A further major advantage of the present invention is the single frangible zone in the stopper. In many designs there is no single point where a breaking feature may be added effectively and two or more components will have to be orchestrated to break under the same applied force to the plunger rod in an attempt to defeat the locking mechanism. In the present invention only one area needs to be weakened and it is centrally located safe from outside manipulation.

An operable syringe assembly having a passive disabling structure includes a barrel having a side wall with an inside surface defining a chamber for retaining fluid, an open proximal end and a distal end including a distal wall having a passageway therethrough in fluid communication with the chamber. An elongate plunger rod includes a proximal end and an open distal end having an interior surface defining a cavity therein with at least one detent on the interior surface of the plunger rod. A secondary cavity is included at the proximal end of the cavity in the plunger rod. The secondary cavity has a distal end and a proximal end and includes a contact surface and at least one discontinuity in the cavity. A stopper includes a sealing element having a peripheral surface forming a seal with the inside surface of the barrel, and a post extending proximally from the sealing element having a proximal end and a distal end. There are at least two post detents on the post. A secondary post extends proximally axially from the proximal end of the post. The secondary post includes a proximal end and a distal end and at least one discontinuity on its surface. The secondary post is positioned at least partially in the secondary cavity of the plunger rod. Structure for limiting motion is provided to allow the stopper to move freely axially with respect to the plunger rod for a limited distance so that the plunger rod can move while the stopper remains stationary in the barrel and for transferring proximally and distally directed forces applied to the plunger rod to the stopper. In some embodiments the distance of this lost motion between the stopper and the plunger rod is determined by the secondary post contacting a contact surface in the secondary cavity of the barrel and the discontinuity on the secondary post contacting the secondary cavity discontinuity in the plunger rod. Any combination of discontinuities in the secondary cavity and/or on the secondary post that provide for a limited distance of lost motion is within the purview of the present invention. A locking element includes a central body portion having an aperture therethrough, at least one cantilevered leg extending distally outwardly from the body portion, and at least one finger element extending inwardly into the aperture. The cantilevered leg includes a sharp-free end directed outwardly for engaging the inside surface the barrel and the inside surface of the plunger rod. The locking element is initially positioned with the sharp-free end contacting the interior surface of the plunger rod proximally of the at least one detent in the plunger rod. The post is positioned in the aperture of the locking element wherein the finger element is contacting the proximal most of the at least two post detents, so that applying a proximally-directed force to the plunger rod while holding the barrel causes the plunger rod to move proximally with respect to the stopper until the free end of the cantilevered leg moves distally along the inner surface of the plunger rod cavity to the at least one detent in the cavity and the structure for limiting motion causes the stopper to move with the plunger rod in a proximal direction for a selected distance. Subsequently applying a distally directed force to the plunger rod to discharge fluid from the chamber causes the plunger rod to move in a distal direction along with the locking element due to its engagement with the at least one detent in the cavity until the structure for limiting motion causes the stopper to move distally along with the plunger rod to discharge fluid from the chamber. Subsequently applying a proximally-directed force to the plunger rod will cause the plunger rod to move proximally with the free end of the cantilevered leg moving relatively distally along the inside surface of the plunger rod past the distal end of the plunger rod so that the cantilevered leg engages the inside surface of the barrel to help prevent proximal movement of the stopper for rendering the syringe assembly unusable.

Other embodiments may include a plunger rod with two axially-spaced detents, and a post with three axially-spaced post detents so that the plunger rod can be moved distally two times before proximal motion of the plunger rod causes the locking element to engage the inside surface of the barrel.

The two axially-spaced detents of the plunger rod may include two axially-spaced steps, each having a blunt surface at its distal end extending inwardly from the interior surface of the plunger rod.

Some or all of the three axially-spaced post detents may include an incline surface extending proximally inwardly and a blunt surface at the distal end of each of the inclined surfaces extending radially inwardly.

The syringe assembly may include a locking element having two cantilevered legs positioned on opposite sides of the central body portion.

The structure for limiting free axial motion of the stopper with respect to the plunger rod may include at least one motion limiting discontinuity on the secondary post positioned to engage at least one motion limiting discontinuity in the secondary cavity. The at least one motion limiting discontinuity on said secondary post may include an outwardly directing projection and the at least one motion limiting discontinuity in the plunger rod secondary cavity may include an inwardly directed projection.

The syringe assembly may include a radial projection or cam surface on the stopper positioned to contact and force the cantilevered leg outwardly when excessive proximal force is applied to the plunger rod in an attempt to overcome the locking element's engagement of the inside surface of the barrel.

The syringe assembly may further include a frangible zone on the stopper which allows the plunger rod to disconnect from the stopper sealing element during application of excessive proximally-directed force to the plunger rod in an attempt to overcome the locking element's engagement of the inside surface of the barrel. The frangible zone may comprise an area of reduced cross-sectional area which is weaker than the post and the secondary post in areas outside of the zone. The frangible zone is positioned within the plunger rod. Only one frangible zone is necessary.

The syringe assembly may have a discontinuity on the inside surface of the barrel side wall positioned to engage the sharp-free end of the locking element when the sharp-free end is in contact with the inside surface of the barrel.

The syringe assembly may include a distal wall on the barrel having an elongate tip extending distally therefrom having a passageway in fluid communication with the passageway with the distal wall of the barrel. The syringe assembly may also further include a needle cannula having a distal end, a proximal end and a lumen therethrough. The proximal end of the needle cannula is connected to the distal end of the barrel so that the lumen is in fluid communication with the passageway.

Another embodiment of an operable syringe assembly of the present invention having passive disabling structure includes a barrel comprising a side wall having an inside surface defining a chamber for retaining fluid, an open proximal end and a distal end including a distal wall having a passageway therethrough in fluid communication with the chamber. An elongate hollow plunger rod having a proximal end, an open distal end and an interior surface defining a cavity is provided. A stopper includes a sealing element with a peripheral surface forming a seal with the inside surface of the barrel and a post projecting proximally from the sealing element. A locking element includes a central body portion having at least one cantilevered leg extending distally outwardly from the body portion. The at least one leg includes a sharp free and directed outwardly for engaging the inside surface of the barrel. The locking element is movably engaged with the post and movably engaged with the plunger rod interior surface. Structure is provided for indexing the locking element distally in the plunger rod during proximal motion of the plunger rod to draw fluid into the chamber and for indexing the locking element distally on the post of the stopper during distally directed motion of the plunger rod for delivering fluid from the chamber through the passageway. Structure is also provided for limiting axial free movement of the stopper with respect to the plunger rod to allow the indexing of the locking element and for applying proximally and distally directed forces to the stopper through the plunger rod.

The locking element may be made of sheet metal such as stainless steel and the stopper may be integrally formed of thermoplastic material.

DETAILED DESCRIPTION OF THE INVENTION

Figure 1:
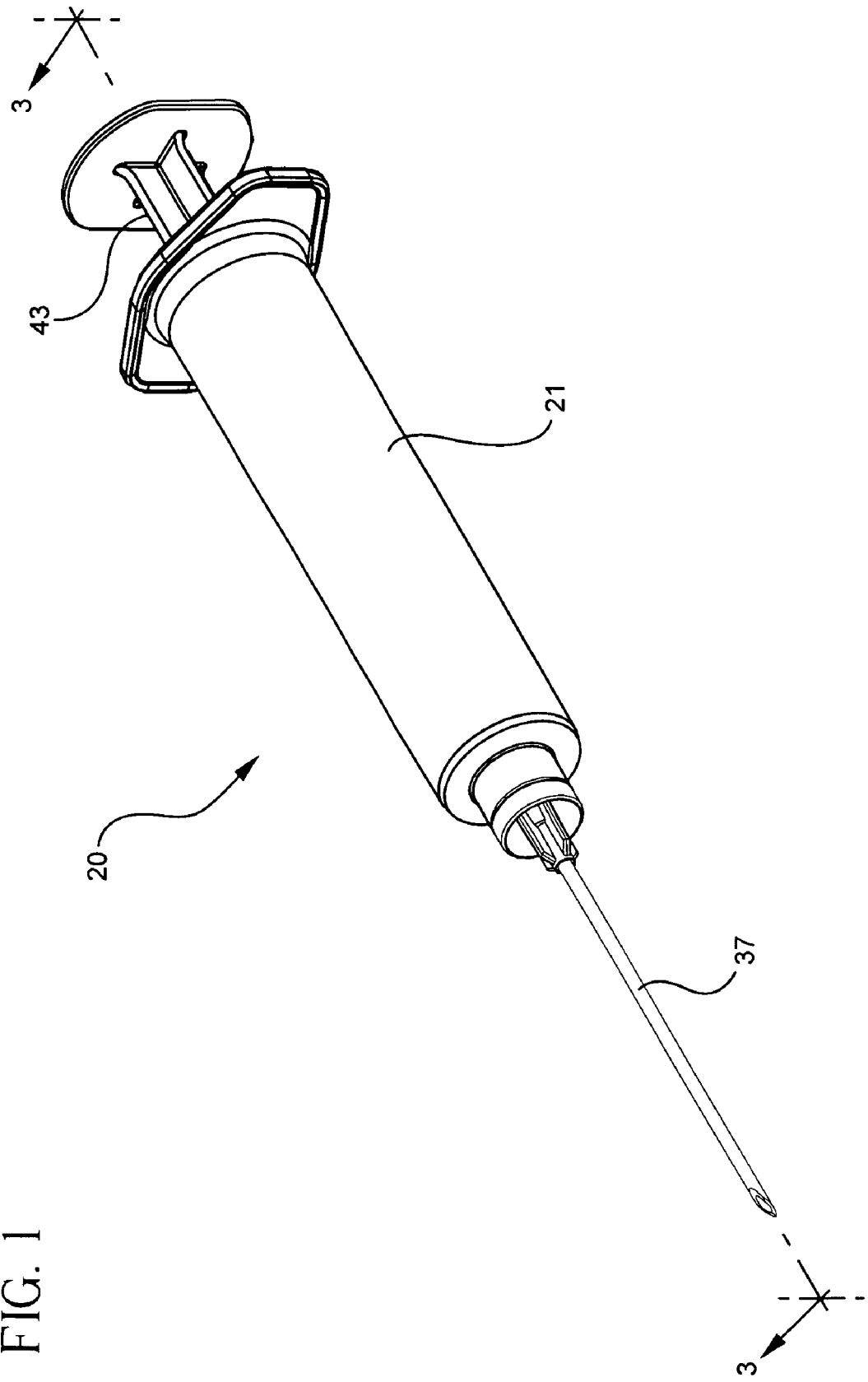
FIG. 1 is a perspective view of the syringe assembly of the present invention.
Figure 2:
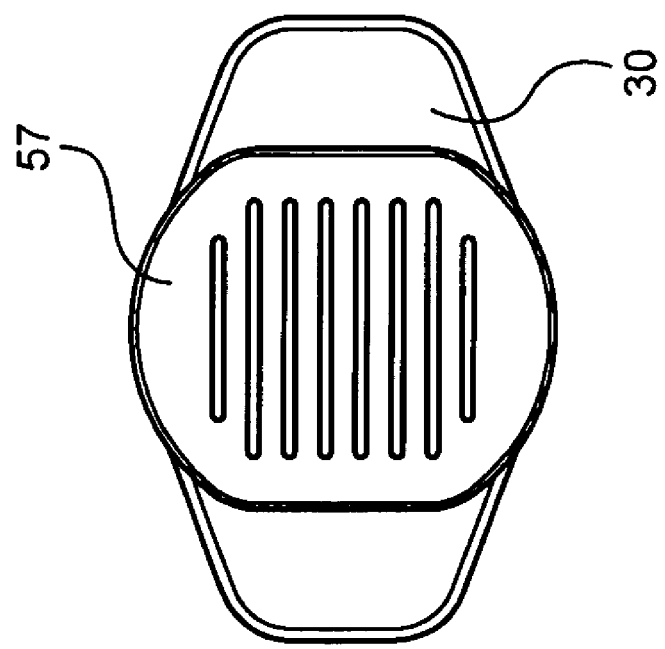
FIG. 2 is a side-elevational end view of the proximal end of the syringe assembly of FIG. 1.
Figure 3:
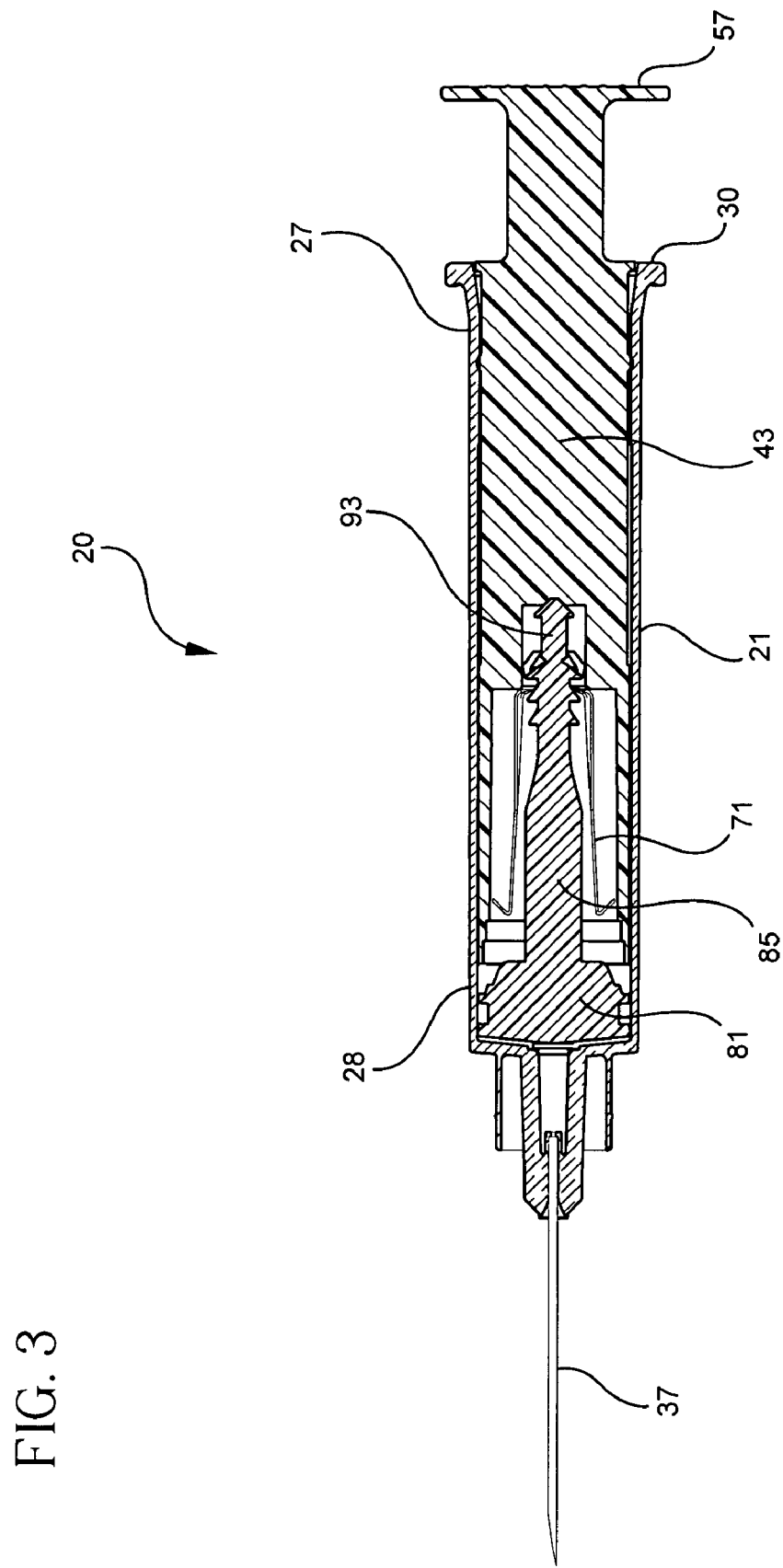
FIG. 3 is a cross-sectional view of the syringe assembly of FIG. 1 taken along line 3-3.
Figure 4:
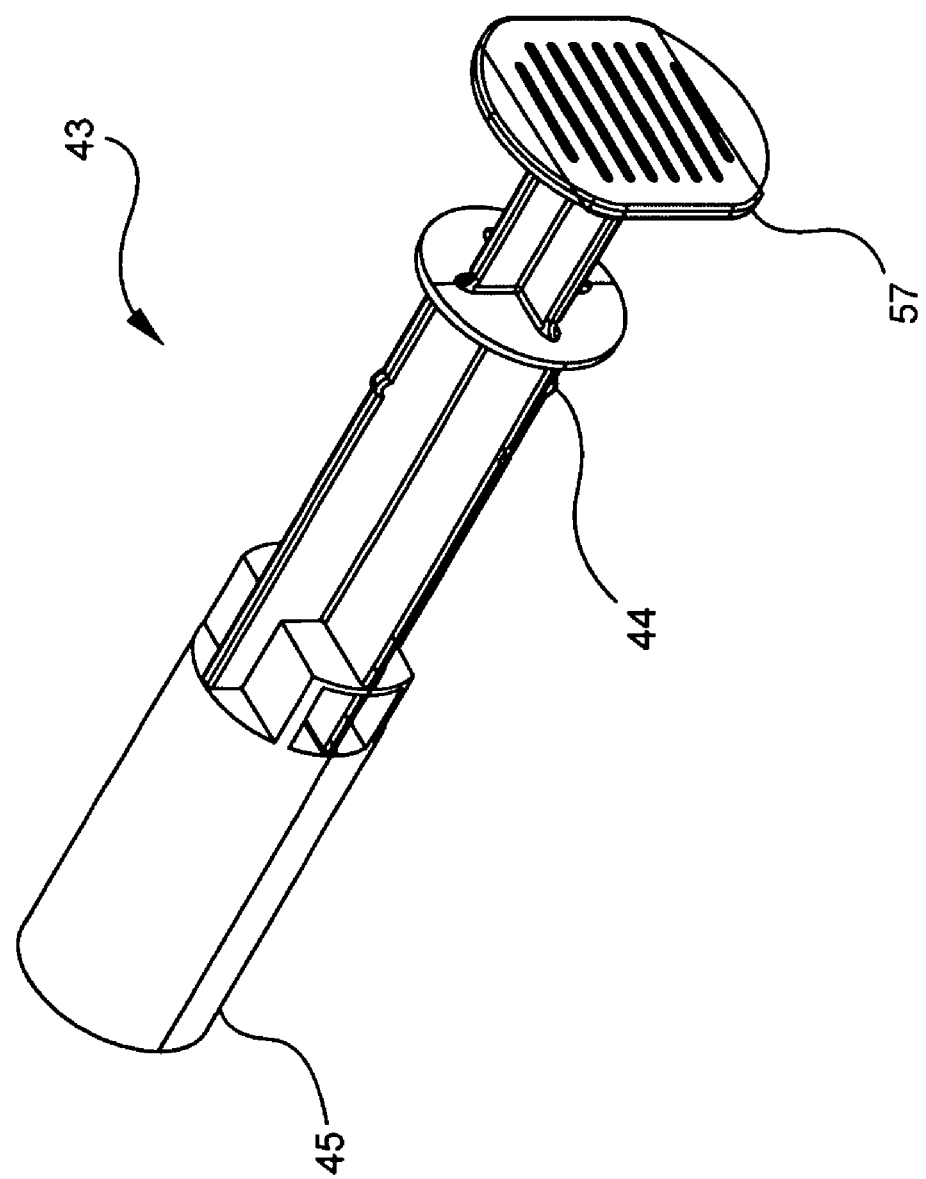
FIG. 4 is a perspective view of the plunger rod of the syringe assembly viewed from its proximal end.
Figure 5:
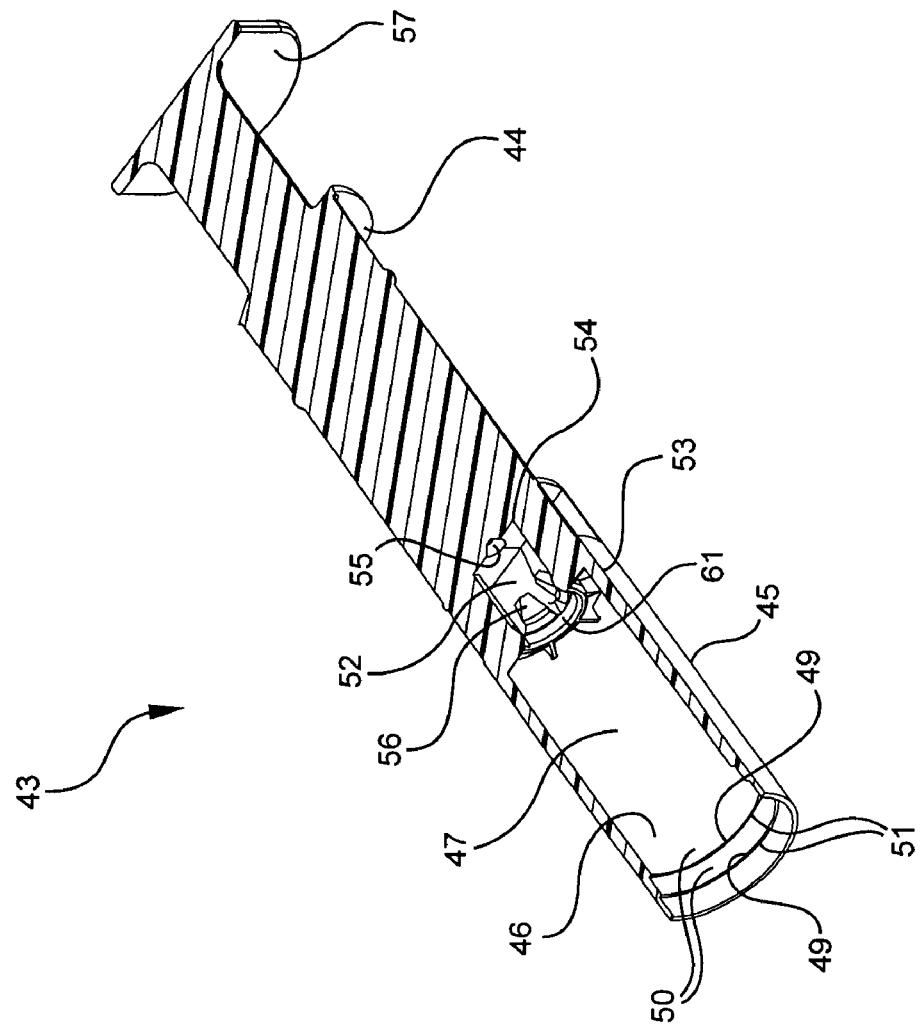
FIG. 5 is a perspective cross-sectional view of the plunger rod viewed from its distal end.
Figure 7:
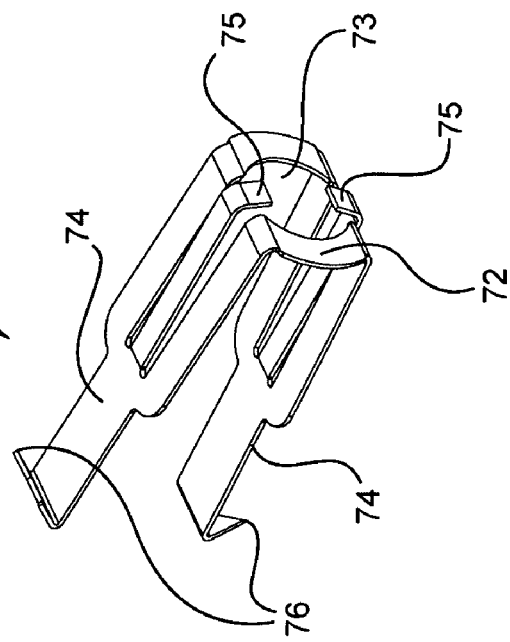
FIG. 7 is a perspective view of the locking element viewed from its proximal end.
Figure 6:
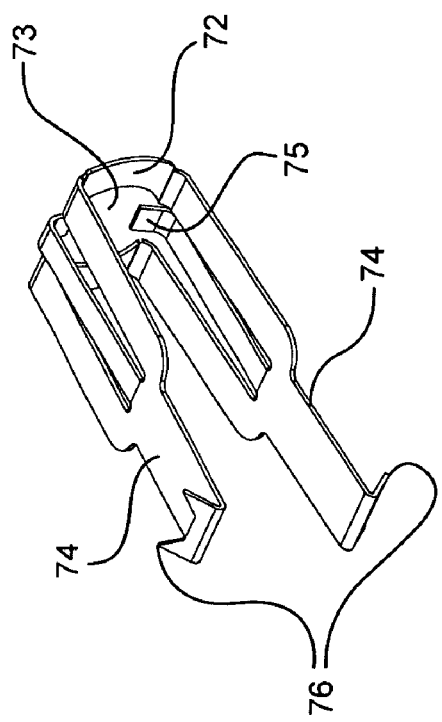
FIG. 6 is a perspective view of the locking element of the syringe assembly viewed from its distal end.
Figure 8:
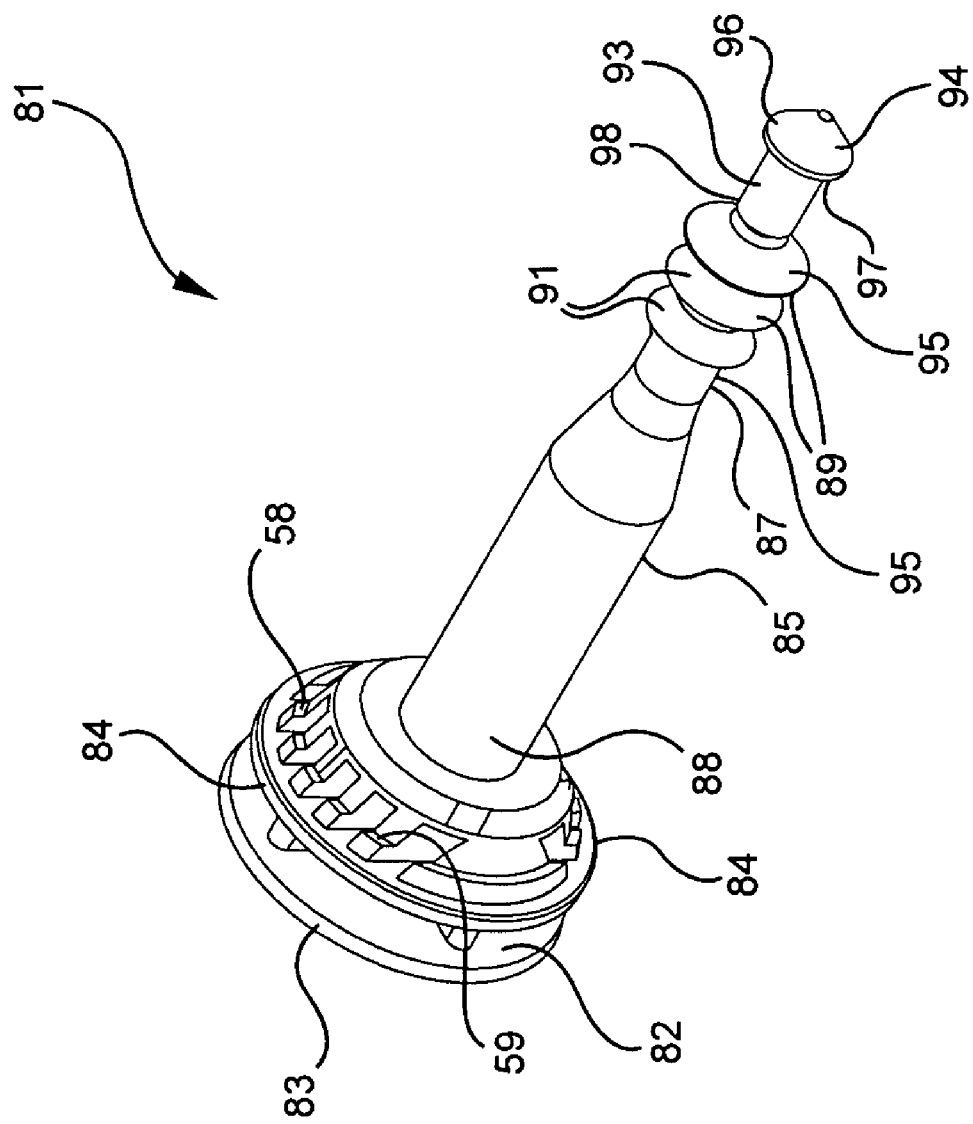
FIG. 8 is a perspective view of the stopper of the syringe assembly viewed from its proximal end.

Referring to FIGS. 1-18, a syringe assembly 20 having passive disabling features includes a barrel 21 and a plunger assembly 22. Barrel 21 includes a cylindrical side wall 23 having an inside surface 24 defining a chamber 25 for retaining fluid. The barrel further includes an open proximal end 27 and a distal end 28 including a distal wall 29 having a passageway 32 therethrough in fluid communication with the chamber. In this embodiment, the distal wall of the barrel includes an elongate tip 31 extending distally therefrom and having a passageway therethrough in fluid communication with the passageway in the distal wall. In this embodiment, barrel 21 also includes a needle cannula 37 having a proximal end 38, a distal end 39 and a lumen 40 therethrough. The proximal end of the needle cannula is attached to elongate tip 31 so that the lumen of the needle cannula is in fluid communication with passageway 32 in the barrel. A needle hub may also be attached to the proximal end of the needle cannula. In this configuration the needle hub engages the elongate tip to establish fluid communication between the lumen and the passageway in the barrel.

Plunger assembly 22 includes an elongate plunger rod 43, a stopper 81 and a locking element 71. Plunger rod 43 includes a proximal end 44, an open distal end 45 and interior surface 46 defining a cavity 47 therein. The interior surface of the plunger rod preferably includes at least one detent. In this embodiment the at least one detent on the interior surface of the plunger rod includes two annular axially spaced detents 49 on the interior surface of the cavity. Each detent comprises a step 50 having a blunt surface 51 at its distal end. As will be explained in more detail hereinafter, the present invention can function without detents on the interior surface of the plunger rod. The plunger rod also includes a secondary cavity 52 at a proximal end of cavity 47. The secondary cavity preferably includes a distal end 53 having a distal contact surface 61, a proximal end 54 having a proximal contact surface 55, and at least one discontinuity therein. In this embodiment the discontinuity comprises one or more inwardly directed projections 56. The secondary cavity is preferably smaller than cavity 47. The primary purpose of the secondary cavity is to interact with the stopper so that the stopper is free to move axially with respect to the plunger rod for a limited distance. As will be seen hereinafter, this lost motion which allows the plunger rod to move independently of the stopper allows the locking element to index through a sequence of positions which end in the locking of the stopper in the barrel to prevent further use.

Stopper 81 includes a preferably circularly-shaped sealing element 82 having a peripheral surface 83 forming a seal with the inside surface of the barrel. A post 85 extends proximally from the sealing element and has a proximal end 87, a distal end 88 and preferably at least two detents on its surface. In this embodiment, the at least two post detents includes three axially-spaced post detents 89. Each post detent preferably but not necessarily, includes an inclined surface 91 and a blunt surface 92 at the distal end of each inclined surface. As will be explained in more detail hereinafter it is within the purview of the present invention to include an embodiment having a post without detents. A secondary post 93 extends proximally axially from the proximal end of post 85. The secondary post includes a proximal end 94, a distal end 95 and at least one discontinuity on its surface. In this embodiment discontinuity 96 is a radial projection having a distally-facing surface 97 thereon. The secondary post is positioned at least partially in the secondary cavity of the plunger rod. As mentioned hereinabove, the plunger rod is free to move axially with respect to the stopper for a limited distance which, in this embodiment, is controlled in one direction by the proximal end of the secondary post contacting proximal contact surface 55 in the secondary cavity and/or the proximal most detent 89 and distal contact surface 61 of the secondary cavity, and in the other direction by the secondary post discontinuity contacting the secondary cavity discontinuity in the plunger rod.

Locking element 71 includes a central body portion 72 having an aperture 73 therethrough. Preferably, at least one cantilevered leg extends distally outwardly from the body portion. In this embodiment, there are two cantilevered legs 74 extending distally outwardly from opposite sides of body portion 72. A plurality of cantilevered legs or other spring and/or resilient structures for engaging the interim surface of the plunger rod and the inside surface of the barrel are within the purview of the present invention. At least one finger element 75 extends inwardly into said aperture. In this embodiment the finger element extends proximally inwardly from the aperture. Each of the cantilevered legs preferably includes a sharp-free end 76 directed outwardly from engaging the inside surface of the barrel. The sharp-free end of the cantilevered leg can be formed in any configuration capable of engaging the inside surface of the barrel, such as a sharp edge or one or more pointed teeth and the like. The locking element may be made of a variety of materials, or combinations of materials, however, it is preferred to have a sharp-free end made of metal, and it is also preferred that the entire locking element be integrally formed from sheet metal such as stainless steel.

Figure 9:
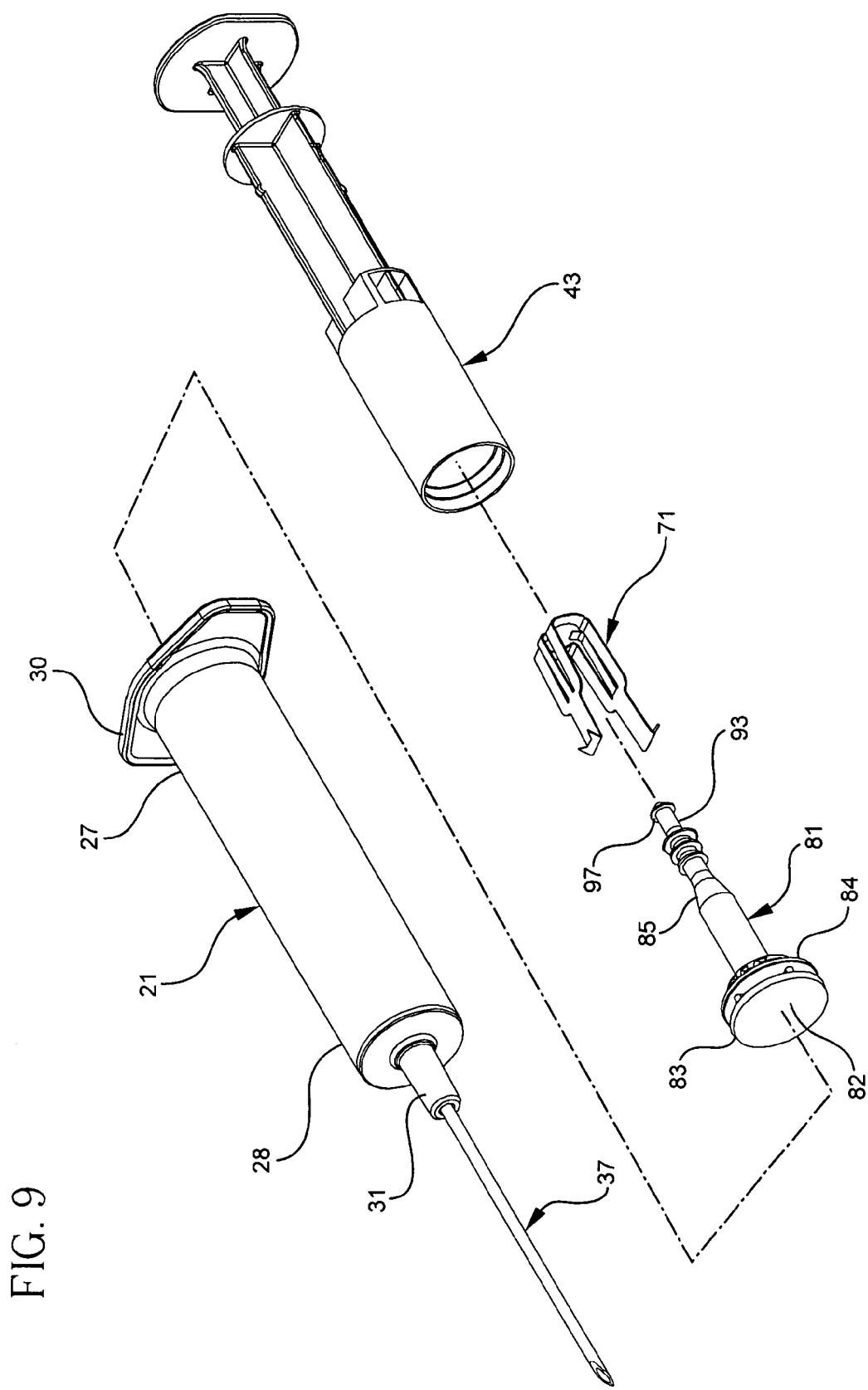
FIG. 9 is an exploded perspective view of the syringe assembly.

In this embodiment, plunger assembly 22 may be assembled by inserting locking element 71 into the distal end of plunger rod 43. The post of stopper 81 is then inserted into the distal end of the plunger rod through aperture 73 of locking element 71 so that cantilevered legs 74 extend towards circularly-shaped sealing element 82 of the stopper as illustrated in FIG. 9. The plunger assembly is then inserted into barrel 21 through open proximal end 27 to the initial position illustrated in FIGS. 3 and 10. Also, the syringe assembly may be assembled by inserting locking element 71 into the distal end of the plunger rod and inserting stopper 81 into the open proximal end of barrel 21, and then inserting the locking element/plunger rod into the proximal end of the syringe barrel.

Figure 10:
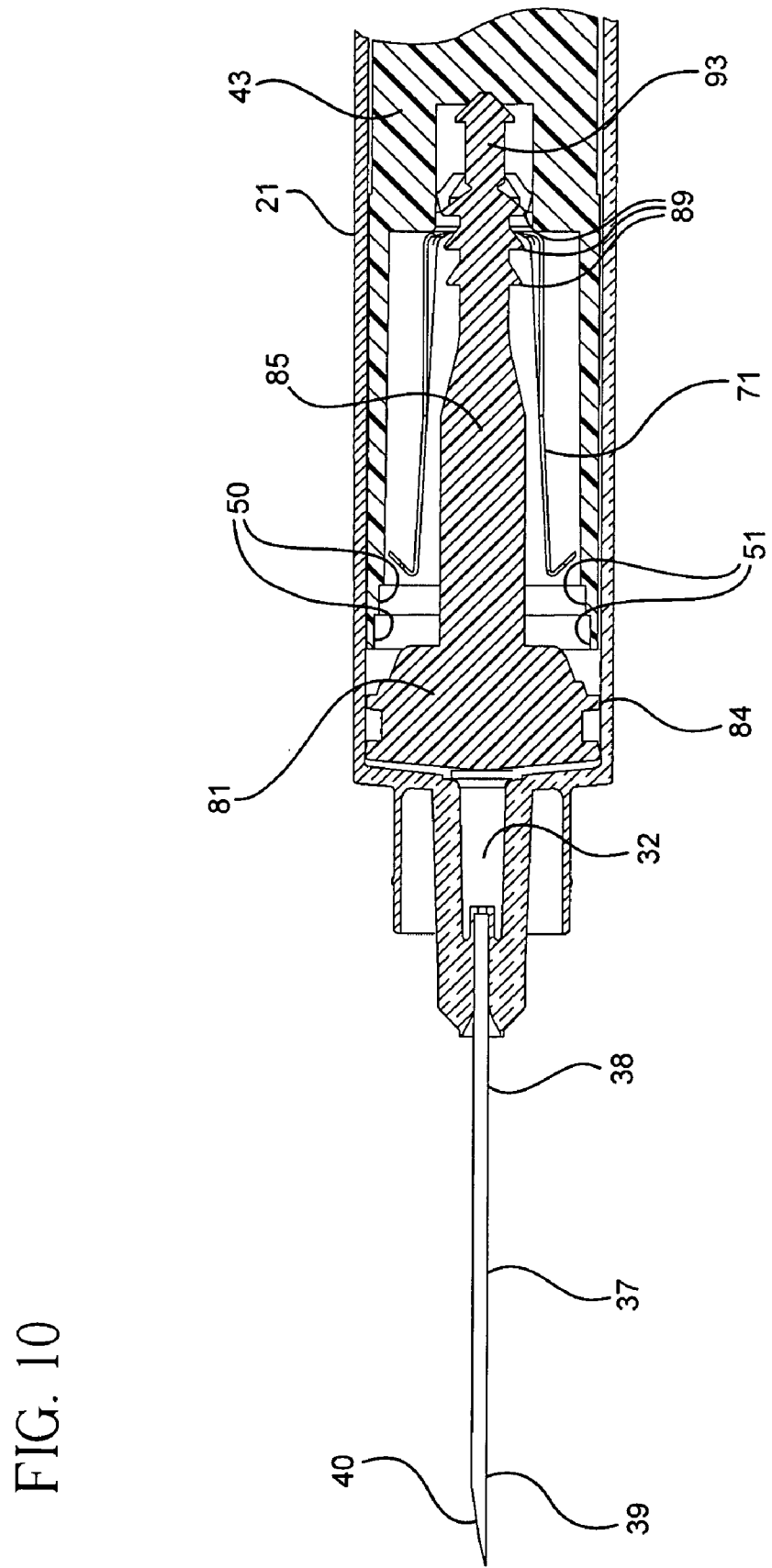
FIG. 10 is an enlarged partial cross-sectional view of the syringe assembly of FIG. 3 showing the syringe assembly before use.

In the initial position of the syringe assembly, locking element 71 is positioned with its sharp-free end 76 contacting the interior surface of the plunger rod proximally of axially-spaced steps 50. Post 85 on stopper 81 is positioned in aperture 73 of locking element 71 so that finger element 75 contacts the post proximally of two of the three axially-spaced post detents 89. The proximal end of the secondary post 93 is near or contacting contact surface 55 in proximal end 52 of the secondary cavity in the plunger rod, and the inclined surface of the most proximal post detent 89 is near or contacting contact surface 61 at the distal end of the secondary cavity. Contact between the proximal end of the secondary post and contact surface 55 in the secondary cavity and/or contact between the proximal most post detent, and contact surface 61 defines the proximal most motion of the stopper with respect to the plunger rod. Both contacts are preferred for stronger resistance to excessive distally directed force on the plunger rod. Stopper 81 further includes stabilizing member 84 positioned proximally with respect to sealing element 82 and having an outer dimension complementing the outer dimension of the sealing element as illustrated in FIG. 10. Stabilizing member 84 has an outer dimension which is preferably less than the sealing element to assist in stabilizing the stopper to maintain the seal between the peripheral surface of the sealing element and the side surface of the barrel, and to maintain the stopper and post alignment substantially parallel to the axis of the syringe barrel.

As will be shown, the operation of the plunger assembly of this embodiment includes a first aspiration stroke followed by a first dispensing or injection stroke, a second aspirating stroke and a final dispensing or injection stroke after which the syringe will become disabled if another aspiration stroke is attempted. The disabling elements prevent or inhibit movement of the stopper in a proximal aspirating direction thereby limiting the function of the syringe assembly to a single use. The number of strokes in this embodiment is controlled by the number of axially-spaced detents in the plunger rod and the number of axially-spaced post detents on the stopper. However, the actual strokes the syringe may make will be determined by the position of the locking element with respect to the detents in the plunger rod and the detents on the stopper at the time of first use. For example, a syringe with two detents in the plunger rod and three stopper post detents on the stopper can be supplied to the user as a syringe capable of two strokes or four strokes. This is an important feature of the invention since a single syringe assembly can be provided with different stroke limitations before disabling.

Figure 11:
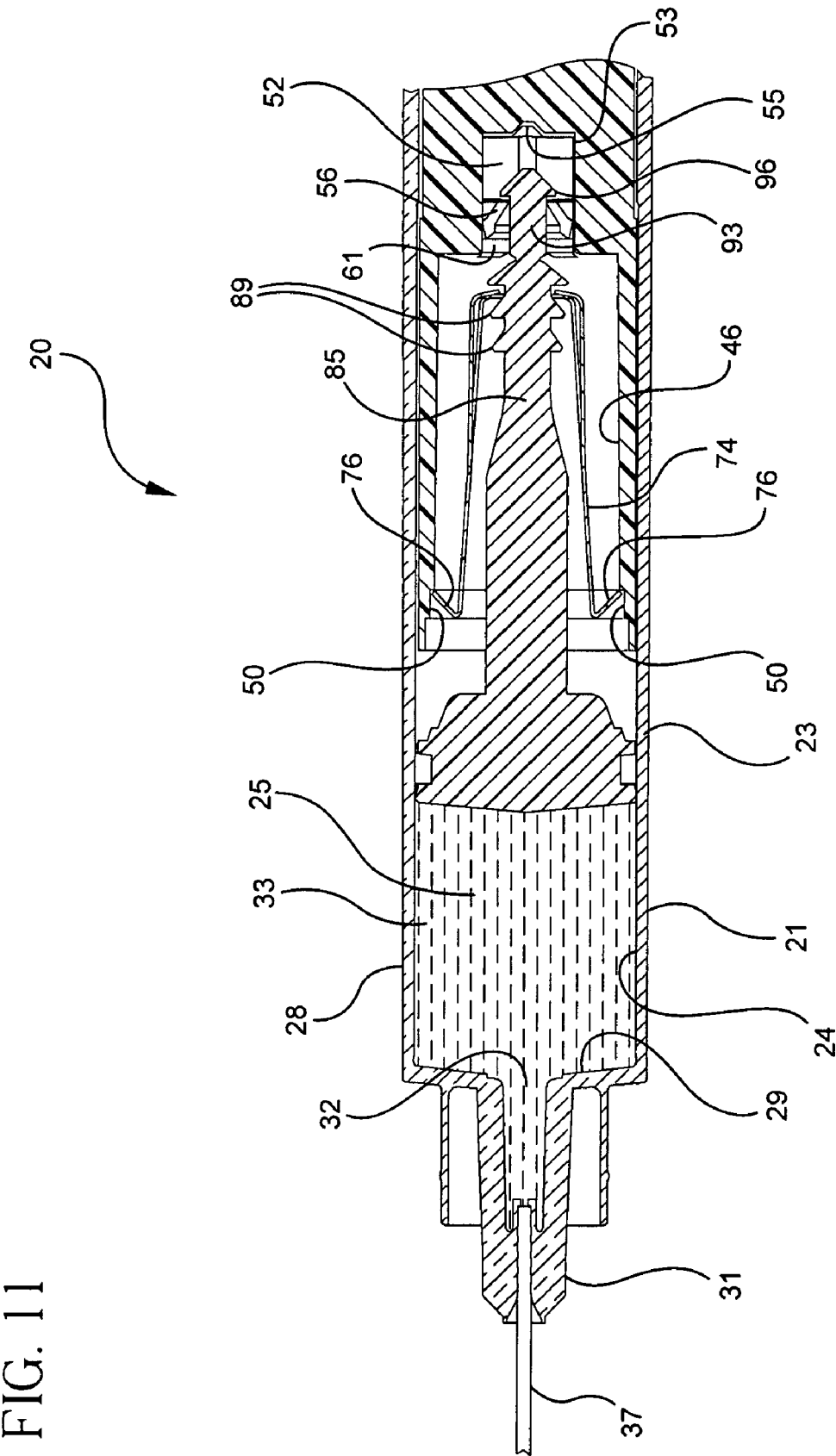
FIG. 11 is an enlarged partial cross-sectional view of the syringe assembly of FIG. 3 showing the syringe assembly after the first aspiration stroke.

Referring to FIG. 11, the syringe assembly may now be used to draw liquid, such as sterile water diluent into the chamber of the barrel by applying a proximally directed force F to a thumb press 57 on the proximal end of the plunger rod while holding the syringe barrel. This causes the plunger rod to move proximally with respect to the stopper until distally-facing surface 97 on discontinuity 96 of the secondary post contacts inwardly-directed projections 56 on the plunger rod. At the same time, the free ends of cantilevered legs 74 move distally along an interior surface 46 of the plunger rod and snap past blunt surface 51 of the proximal-most axially-spaced steps 50. The stopper can now be moved proximally, through action of the plunger rod, until the desired volume is in the chamber, as determined by the user. It is an important feature of this invention that the user determines the volume, rather than the structure of the disabling mechanism dictating the volume as in some prior art devices.

Figure 12:
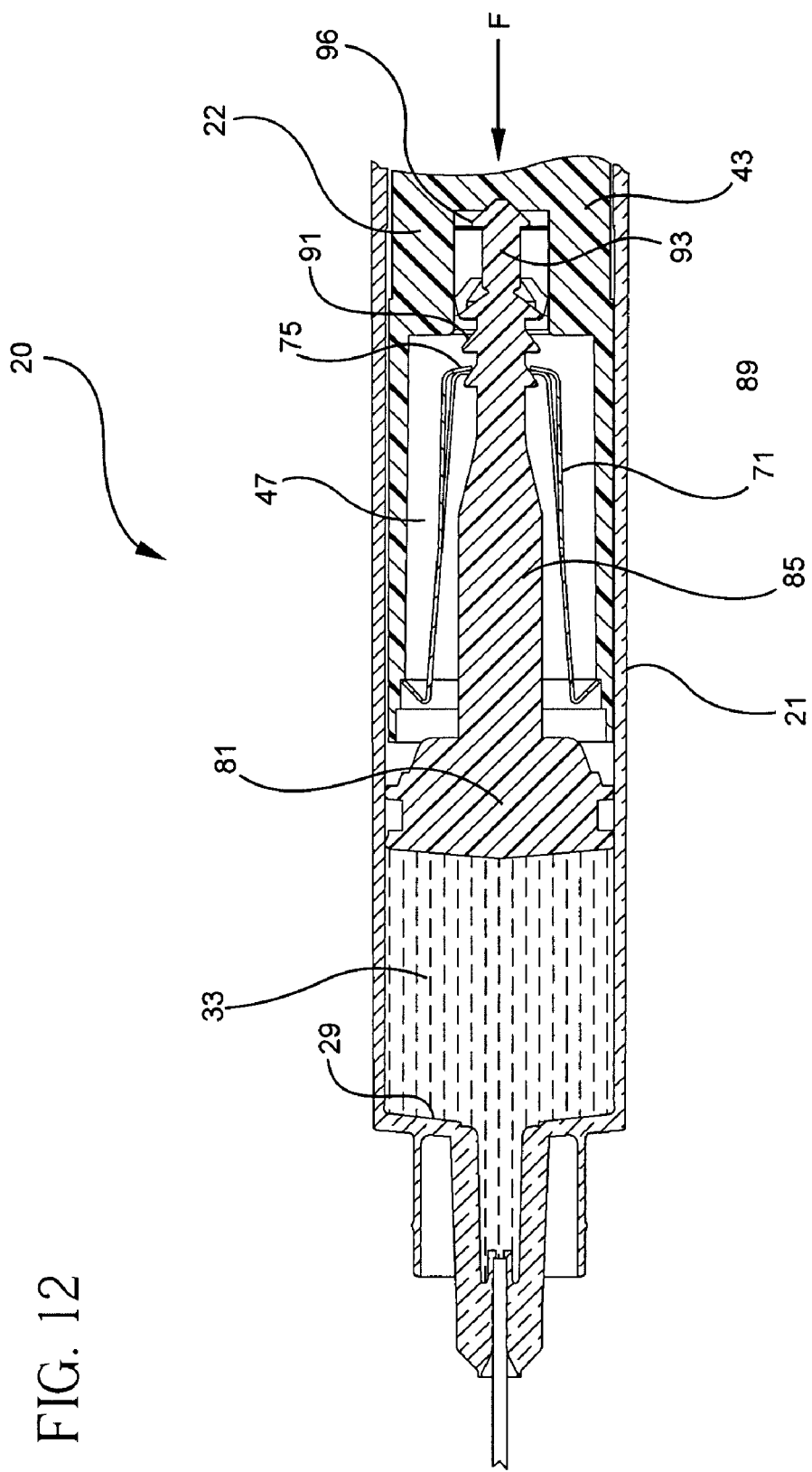
FIG. 12 is an enlarged partial cross-sectional view of the syringe assembly of FIG. 3 showing the syringe assembly during a first dispensing stroke.

Liquid diluent 33 in the chamber may now be dispensed into a vial of dry medication such as lyophilized medication, for reconstitution. As illustrated in FIG. 12, the first dispensing stroke is accomplished by applying force F to the plunger rod, in a distal direction, while holding the barrel. A barrel flange 30 is provided on the proximal end of the barrel to help control motion of the barrel during use of the syringe assembly. As the plunger rod moves distally, locking element 71 moves with the plunger rod dragging the locking element with it so that finger element 75 on the locking element slides from the proximal-most to the next proximal-most detent by riding up inclined surface 91 and falling into second of three post detents 89. When the plunger rod contacts the stopper by action of the proximal end of the secondary post and contact surface 55 in the plunger rod and/or the proximal most post detent and contact surface 61, the stopper will begin moving in a distal direction along with the plunger rod to dispense liquid diluent from the chamber into, for example, a vial of lyophilized medication.

Figure 13:
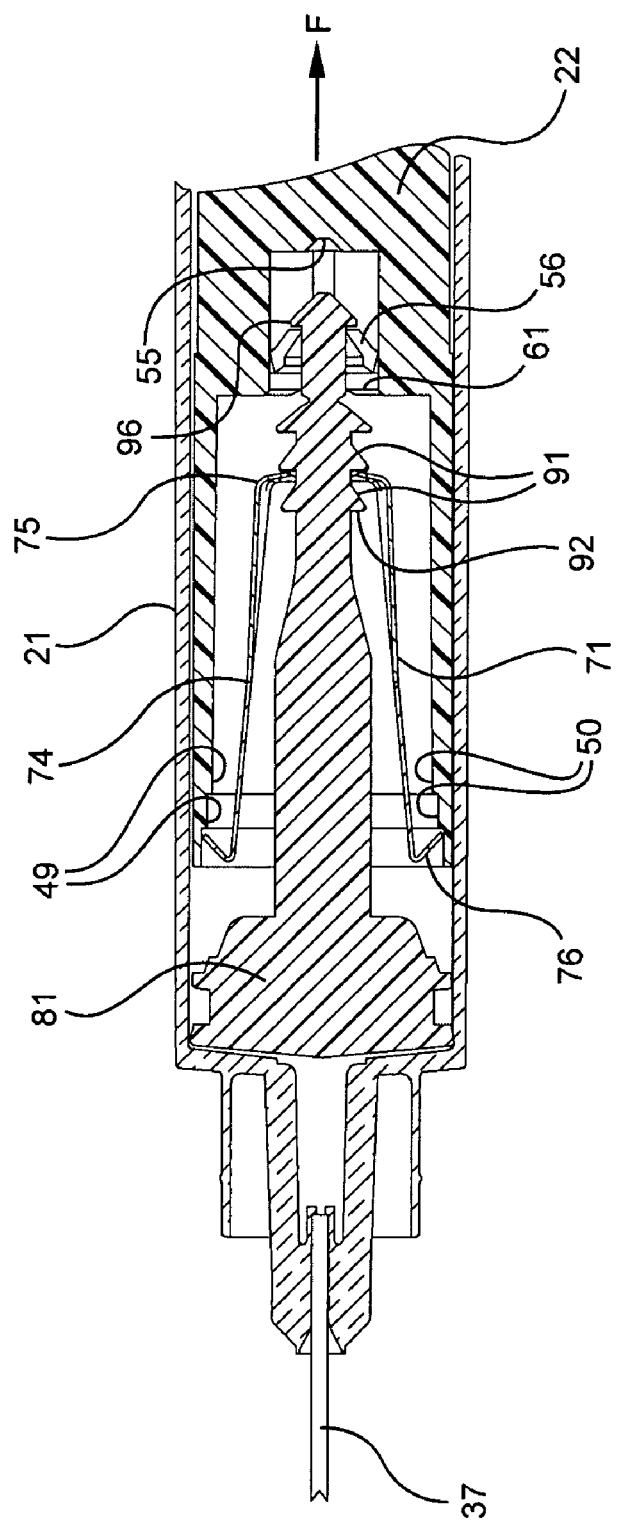
FIG. 13 is an enlarged partial cross-sectional view of the syringe assembly of FIG. 3 showing the syringe assembly at the start of a second aspiration stroke.
Figure 14:
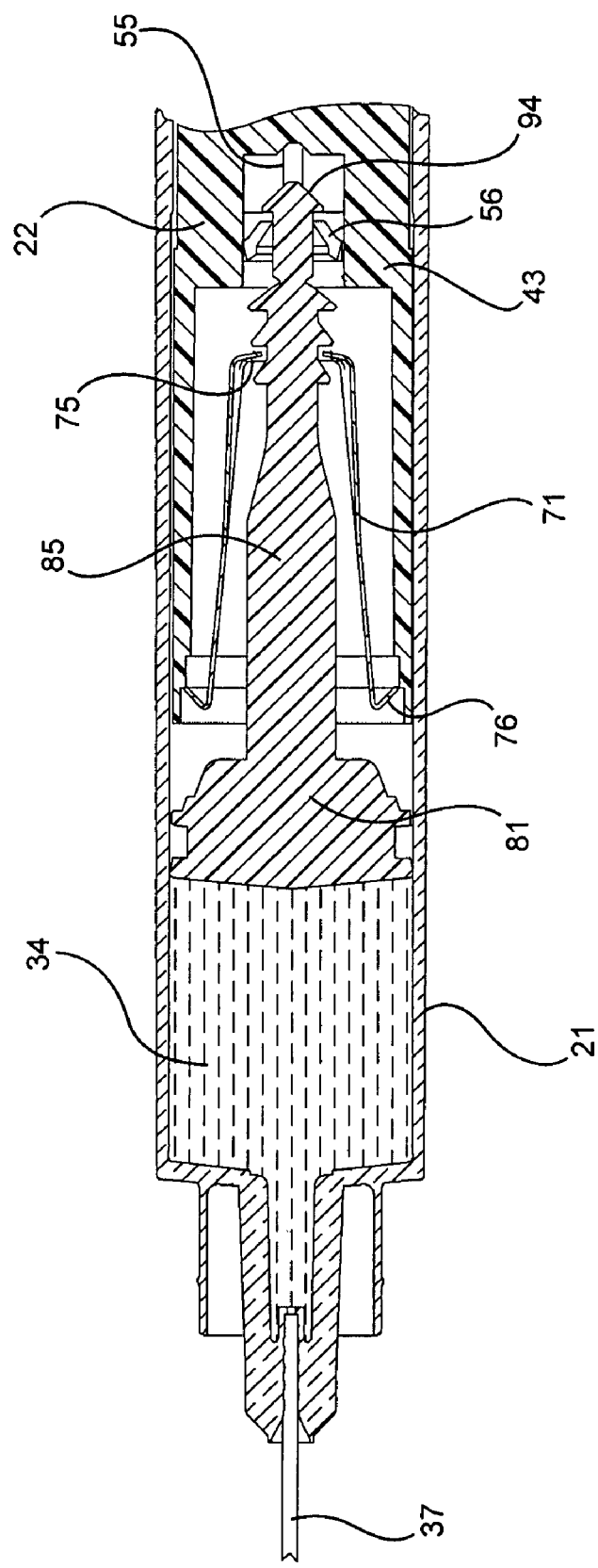
FIG. 14 is an enlarged partial cross-sectional view of the syringe assembly of FIG. 3 showing the syringe assembly after a second aspiration stroke.

When the diluent and the lyophilized medication are mixed, the syringe assembly of the present invention may now be used to withdraw the reconstituted, ready-to-inject medication into the chamber of the syringe barrel, as best illustrated in FIGS. 13 and 14. By applying a proximally-directed force F to the plunger rod while holding the syringe barrel, the plunger rod will move in a proximal direction while locking element 71 will remain relatively stationary due to its connection to the post detent on the stopper. Proximal motion of the plunger rod causes the locking element to move relatively distally along the inside surface of the plunger rod so that the sharp-free ends 76 of the cantilevered legs move from the proximal-most axially-spaced step 50 in the plunger rod to the second more-distal axially-spaced step 50. Proximal motion of the plunger rod also causes distally-facing surface 97 on discontinuity 96 of the secondary post to contact inwardly-directed projections 56 in the secondary cavity so that the stopper now moves proximally with the plunger rod drawing reconstituted medication 34 into chamber 25 of the syringe barrel to an amount determined by the user. The amount of medication drawn into the chamber, and therefore the maximum amount of medication that can be delivered, is determined by the user at the time of use and not by the placement of the components at the time of manufacture.

Figure 15:
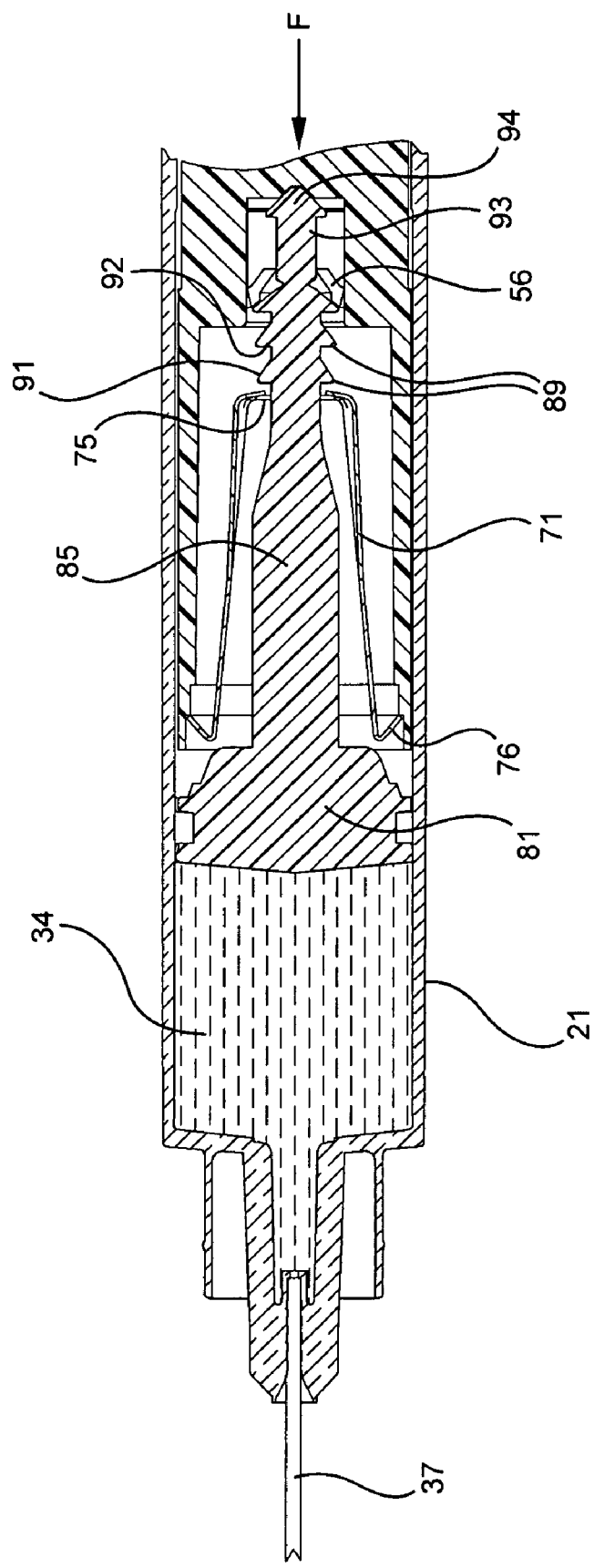
FIG. 15 is an enlarged partial cross-sectional view of the syringe assembly of FIG. 3 showing the syringe assembly during a second dispensing stroke.
Figure 16:
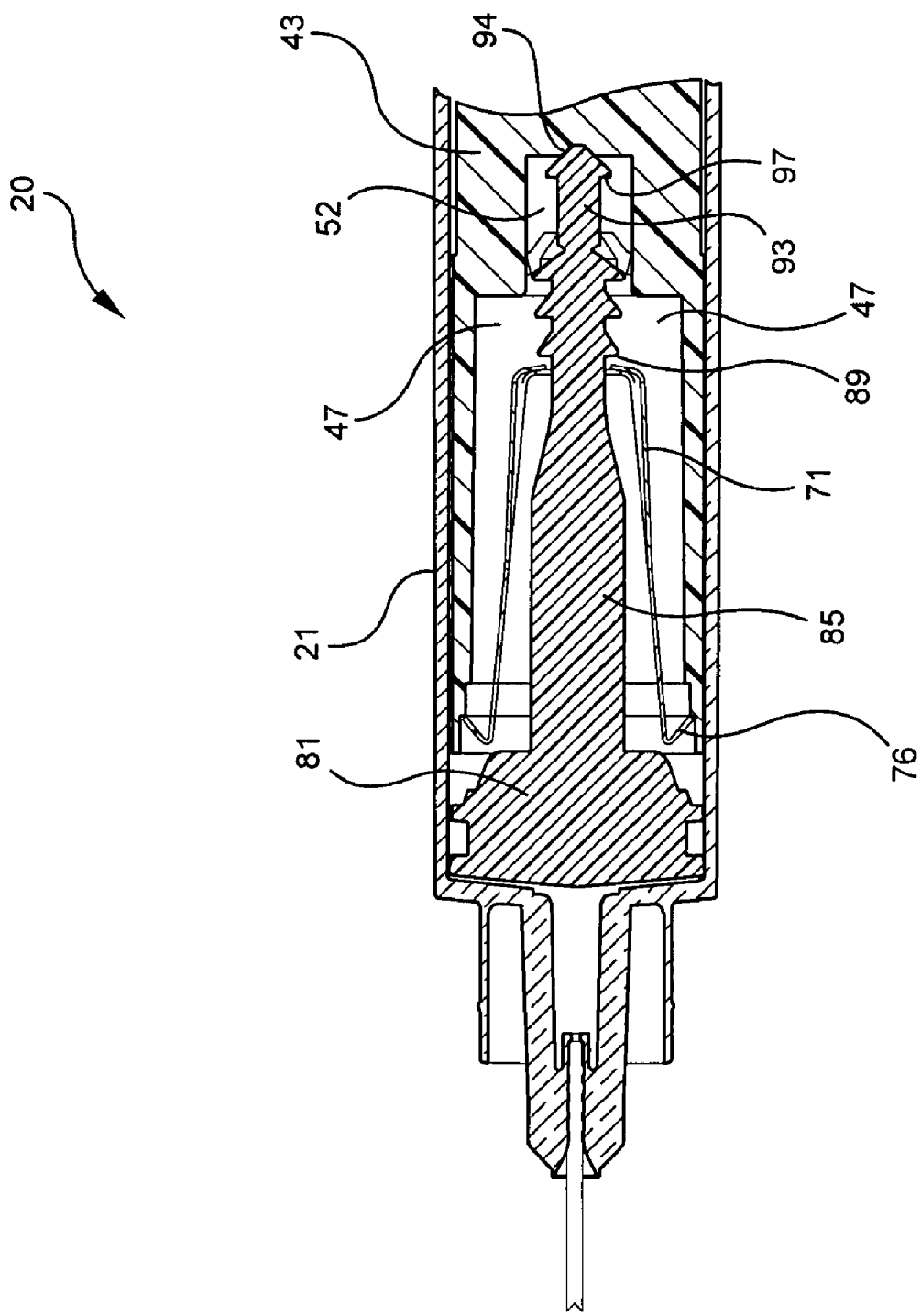
FIG. 16 is an enlarged partial cross-sectional view of the syringe assembly of FIG. 3 showing the syringe assembly after a second dispensing stroke.

The syringe assembly of the present invention is now ready for a second and final dispensing or injection stroke which is best illustrated in FIGS. 15 and 16. Medication 34 is delivered to the patient by applying a distally-directed force F to the plunger rod causing the plunger rod to move in a distal direction with respect to the barrel. As the plunger rod advances in a distal direction engagement of sharp-free ends 76 of the locking element with the most distal blunt surface 50 of axially-spaced steps 50 moves the locking element distally so that finger element 75 of the locking element rides over the distal-most inclined surface 91 of the post detents distally to the most distal post detent 89. When the distally-moving plunger rod contacts the stopper, both the stopper and plunger rod move toward the distal end of the barrel to dispense the contents of the chamber through the passageway.

Figure 17:
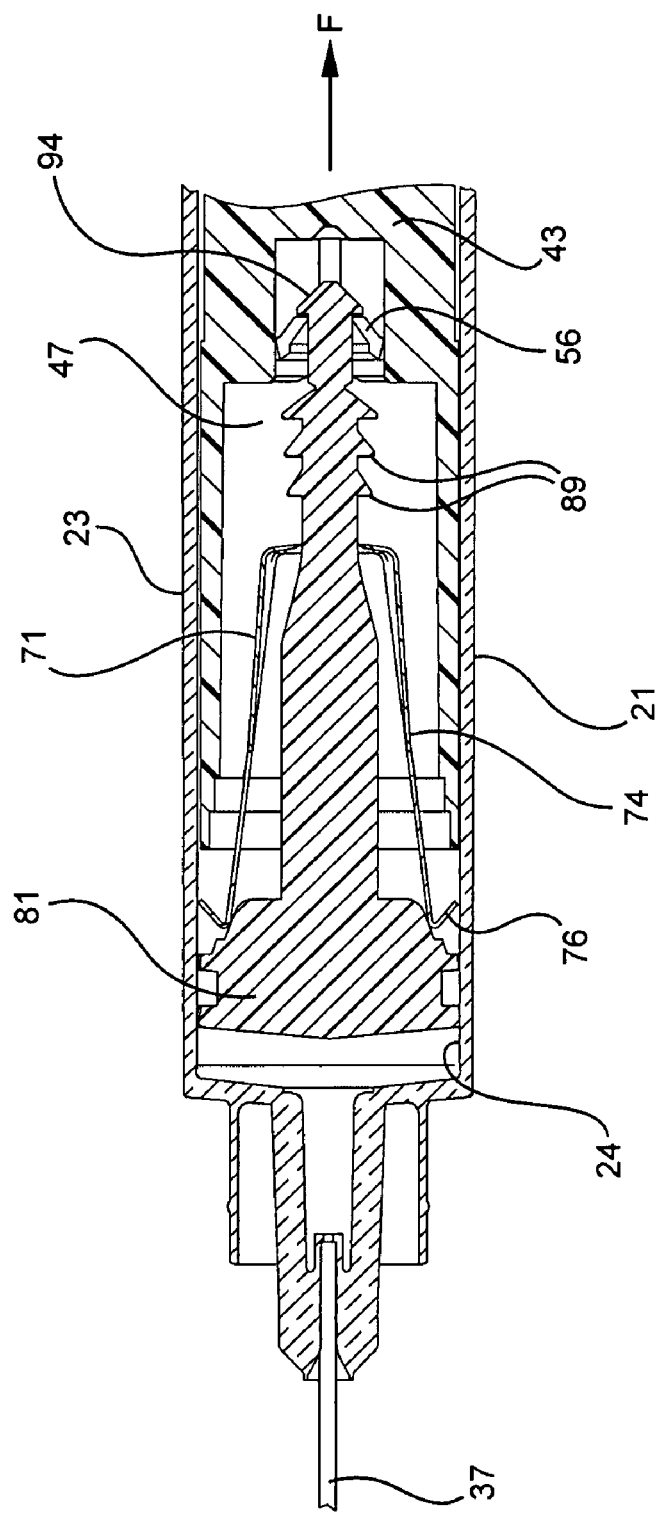
FIG. 17 is an enlarged partial cross-sectional view of the syringe assembly of FIG. 3 showing a position of the internal components including additional structure for preventing reuse in the event of an attempt to withdraw the plunger rod after the second dispensing stroke.
Figure 18:
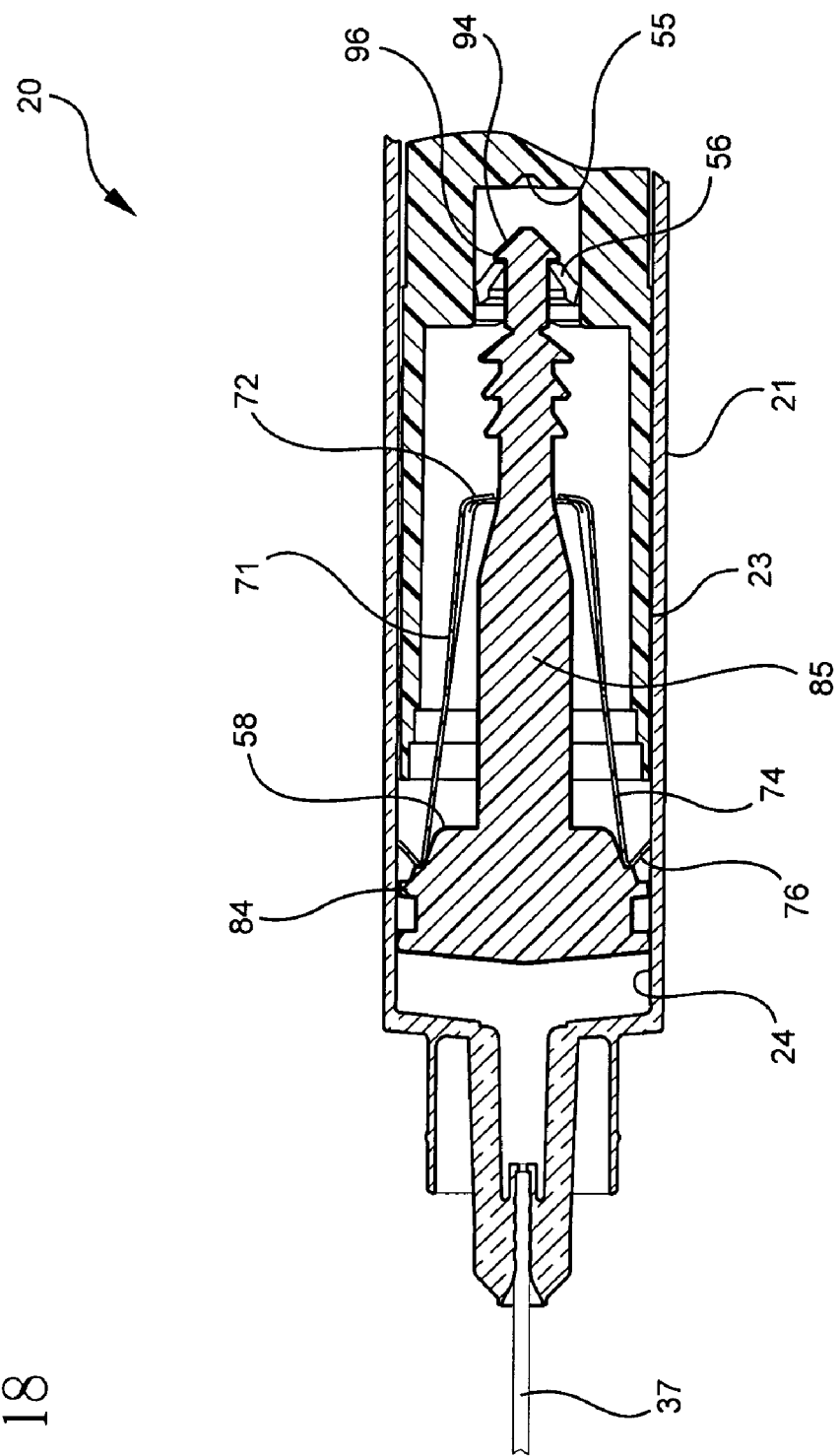
FIG. 18 is an enlarged partial cross-sectional view of the syringe assembly of FIG. 16 showing the further interaction of the additional structure to prevent reuse.

The syringe assembly has now been used and is ready to be discarded. Any attempt to move the plunger rod in a proximal direction with respect to the barrel to refill the syringe assembly for further use will cause the locking element to disable the syringe. Specifically, as best illustrated in FIGS. 17 and 18, applying force F to the plunger rod in a proximal direction will allow the plunger rod to move a short distance until the sharp-free ends 76 of the locking element snap past the distal end of the plunger rod and engage inside surface 24 of barrel 21. In addition, a radial projection in the form of cam surface 58 on the stopper is positioned to force sharp-free ends 76 of the locking element further into the syringe barrel wall as more proximally-directed force is used in an attempt to improperly reuse the syringe. The cam surface may be annular or there may be one or more individual cam surfaces positioned to contact the locking element cantilevered legs. Cam surface 58 also includes a stop 59 to limit the distance the stopper moves in a proximal direction which helps prevent the reuse of the syringe. It is desirable to limit the proximal motion of the stopper to a distance that will only allow the syringe to take in a volume of less than 10% of the medication dose. Accordingly, increased force to pull the plunger rod out of the syringe barrel results in increased force of engagement of the sharp-free ends of the locking element into the barrel.

Figure 19:
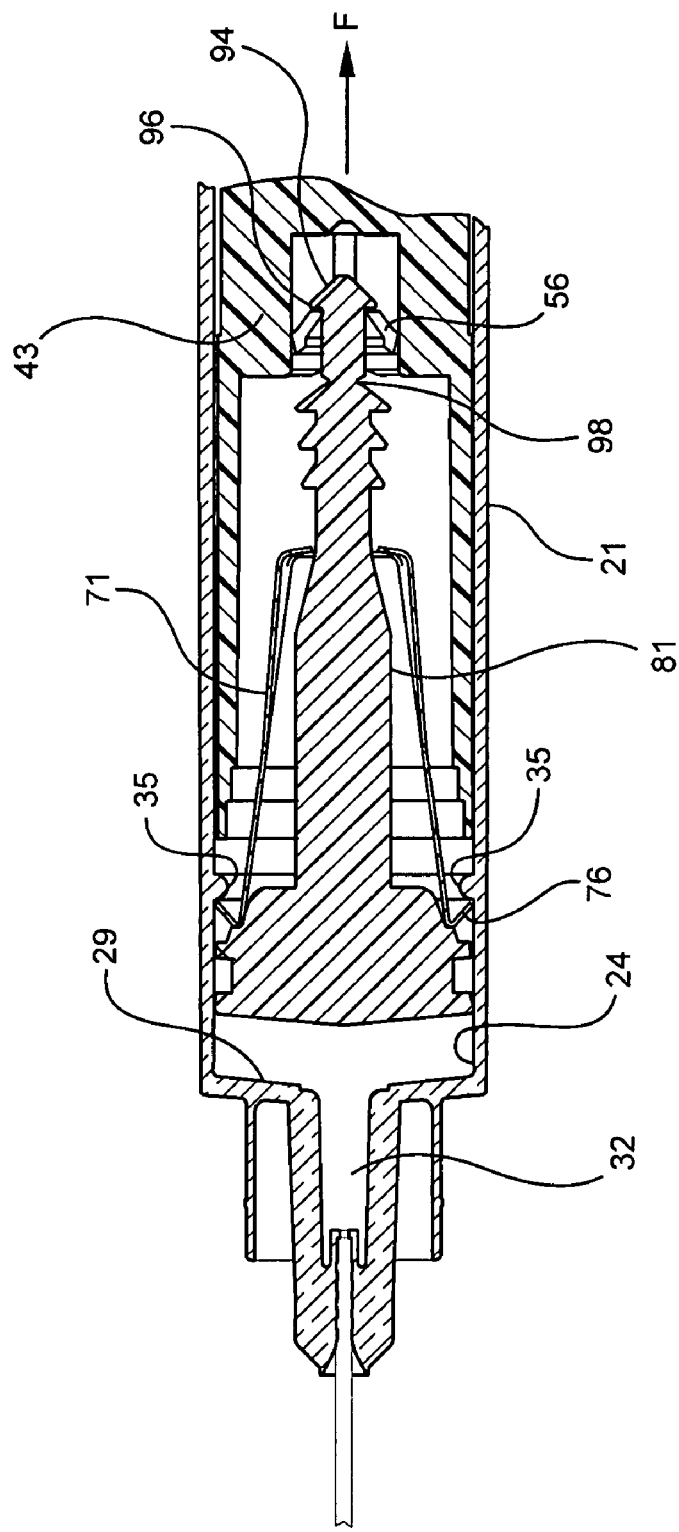
FIG. 19 is an enlarged partial cross-sectional view similar to the syringe assembly of FIG. 18 showing a discontinuity in the syringe barrel for engaging the locking element.

It is also within the purview of the present invention to provide a discontinuity, such as a recess or projection, on the interior surface of the barrel, as illustrated in FIG. 19 to further improve the engagement of the sharp-free end of the locking element with the interior surface of the barrel. In FIG. 19, syringe barrel 21 includes a barrel discontinuity in the form of an inwardly-directed projection 35 on inside surface 24 of the barrel. In this embodiment, projection 35 is an annular ring projecting into the barrel and extending 360° around the inside surface. The discontinuity may be in the form of an annular projection, an annular recess or one or more projections or recesses shaped to engage sharp-free ends 76 of locking element 71 to further increase the grip of the locking element on the inside surface of the barrel.

Figure 20:
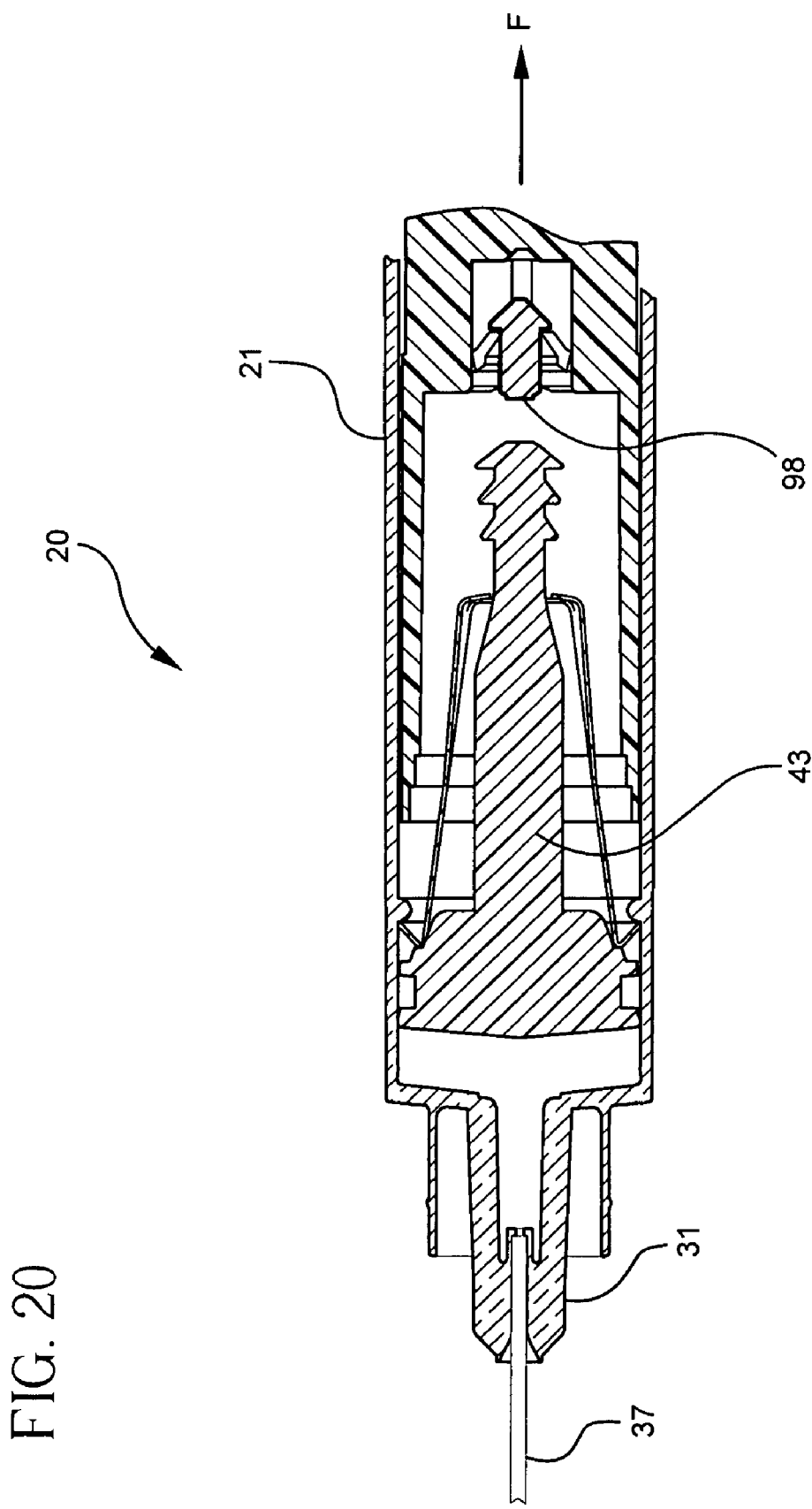
FIG. 20 is an enlarged partial cross-sectional view of the syringe assembly of FIG. 19 showing the breaking of the stopper at a frangible zone.

The syringe assembly of the present invention also includes a frangible zone on stopper 81 positioned distally from discontinuity 96 on secondary post 93 for allowing the plunger rod to disconnect from the stopper sealing element during the application of excessive, proximally-directed force to the plunger rod in an attempt to overcome the locking element's engagement of the inside surface of the barrel. As illustrated in FIGS. 19 and 20, the frangible zone in this embodiment preferably comprises a zone of reduced cross-sectional area 98 which is weaker in tension than the post 85 and secondary post 93 in areas outside of the zone. It should be noted that the frangible zone can be achieved in many ways such as forming portions of the stopper separately and assembling them using adhesive or mechanical connector in the area of the frangible zone, altering the area of the zone to be weaker than surrounding material, forming the stopper of different materials using the weakest material to form the zone and the like. The zone of reduced cross-sectional area illustrated herein is merely representative of these many possibilities all of which are in the purview of the present invention. The frangible zone is an important feature of the present invention since the weakest area of the syringe assembly can be located in one position and carefully controlled for the force of breaking or disconnecting, without needing to compromise other elements of the syringe assembly by having to create multiple frangible zones. The frangible zone is also preferably located within the plunger rod where it is difficult to access from outside of the syringe barrel for the purpose of defeating the single-use structure of the syringe assembly.

Figure 21:
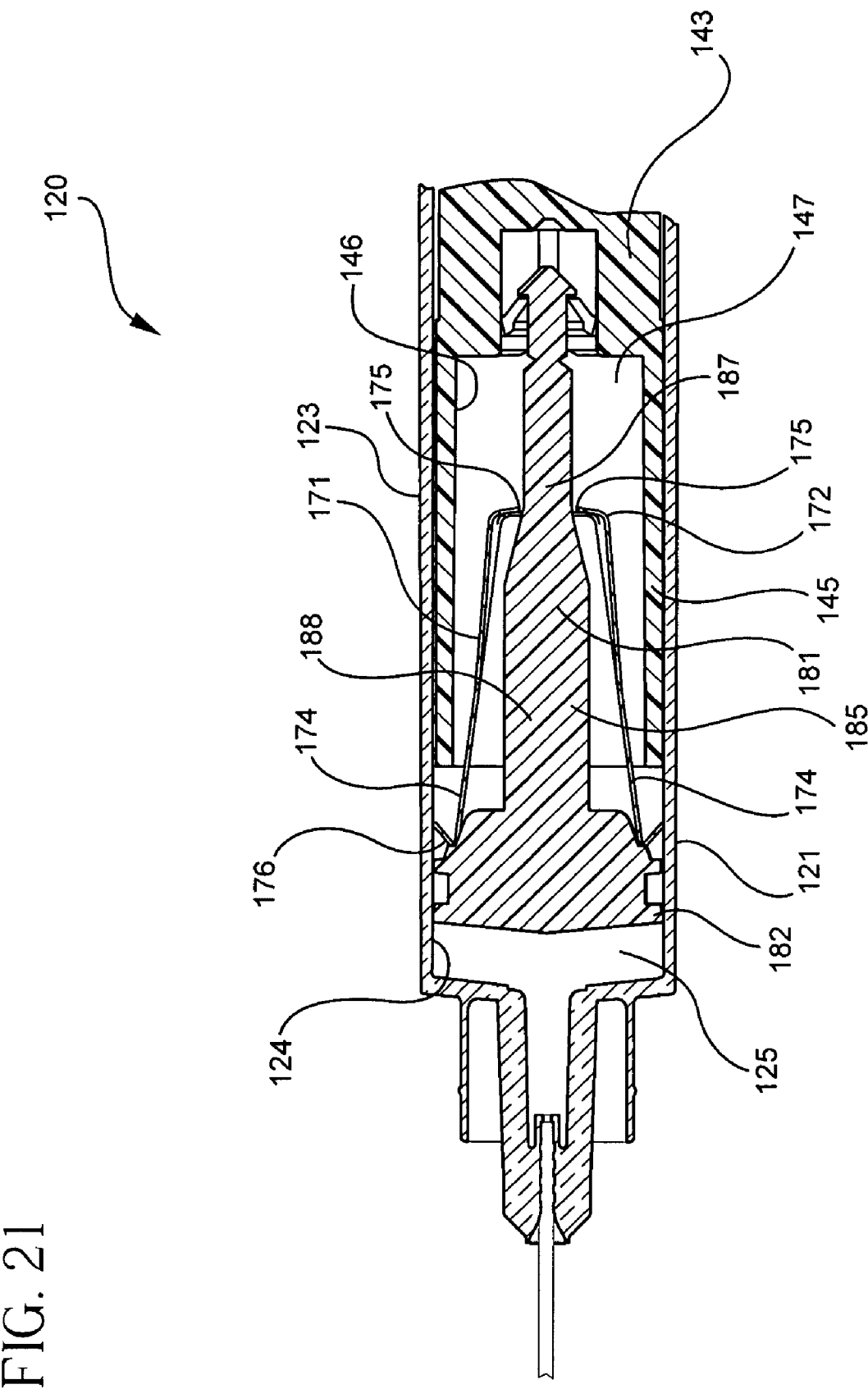
FIG. 21 is an enlarged partial cross-sectional view of an alternative embodiment of the syringe assembly of the present invention.

Referring to FIG. 21, an alternative embodiment of the syringe assembly of the present invention is illustrated. This embodiment functions similarly to the embodiment of FIGS. 1-18 with the exception that there are no detents on the stopper post or in the plunger rod cavity. As described above, embodiments of FIGS. 1-18 include a barrel having a relatively smooth inside surface to which the sharp-free ends of the cantilevered legs of the locking element engage. In the embodiments shown in FIGS. 19 and 20 the barrel includes an inwardly-directed projection. The purpose of this projection is to improve the grip of the free ends of the cantilevered legs on the inside surface of the barrel to more strongly resist the application of a proximally-directed force on the plunger to defeat the locking mechanism after the syringe has been used. If the sharp-free ends of the cantilevered legs are sharp enough and angled properly they should be able to resist such force without addition of an inwardly-directed projection on the inside surface of the barrel. Likewise, the detents on the stopper post and the interior surface of the plunger rod in the embodiment of FIGS. 1-18, are provided to assure that locking element will index properly with each stroke of the plunger with respect to the barrel placing the locking element in position to disable the syringe at the completion of the last delivery stroke. Detents also allow more latitude in the design of the plunger rod, stopper and locking element such as being able to use a broader range of materials, and to use looser, more cost-effective tolerances. However, the invention will function without detents on the stopper post and in the plunger rod if an adequately sharp and resilient element is used with compliant materials. Specifically, as shown in FIG. 21, syringe assembly 120 includes a barrel 121 having a cylindrical side wall 123 and an inside surface 124 defining a chamber 125 for retaining fluid. An elongate plunger rod 143 includes an open distal end 145 having an interior surface 146 defining a cavity 147 therein. A stopper 181 includes a sealing element 182 having a peripheral surface forming a seal with the inside surface of the barrel. A post 185 extends proximally from the sealing element having a proximal end 187 and a distal end 188. Locking element 171 includes a central body portion 172 having an aperture therethrough. Cantilevered legs 174 bend distally-outwardly from opposite sides of body portion 172. At least one finger element 175 bends proximally-inwardly from the aperture. Each of the cantilevered legs has a sharp free end 176 directed outwardly for engaging inside surface 124 of the barrel and interior surface 146 of the plunger rod. The sharp free end of each cantilevered leg is configured to move relatively freely in a distal direction and to resist proximally-directed motion by engaging the surface which is contacts. Likewise, finger element 175 is configured to move distally along the post of the stopper but to resist proximal motion along the post by engaging the stopper post. In all other aspects this embodiment functions similarly to the embodiment of FIGS. 1-18.

While various embodiments have been chosen to illustrate the invention, it will be appreciated that changes and modifications can be made without departing from the scope of the invention.

What is claimed is:

1. An operable syringe assembly having passive disabling structure comprising:
    a barrel including a side wall having an inside surface defining a chamber for retaining fluid, an open proximal end and a distal end including a distal wall having a passageway therethrough in fluid communication with said chamber;
    an elongate plunger rod including a proximal end and an open distal end having an interior surface defining a cavity therein, at least one detent on said interior surface at said distal end of said plunger rod, a secondary cavity at a proximal end of said cavity, said secondary cavity having a distal end and a proximal end, said secondary cavity having a contact surface and at least one discontinuity in said secondary cavity;
    a stopper including a sealing element having a peripheral surface forming a seal with said inside surface of said barrel, a post extending proximally from said sealing element having a proximal end and a distal end, at least two post detents on said post, a secondary post extending axially from said proximal end of said post, having a proximal end and a distal end and at least one discontinuity on its surface, said secondary post being positioned at least partially in said secondary cavity;
    at least one motion limiting discontinuity on said secondary post positioned to engage said at least one discontinuity in said secondary cavity; and
    a locking element including a central body portion having an aperture therethrough, at least one cantilevered leg extending distally outwardly from said body portion, and at least one finger element extending proximally inwardly into said aperture, said at least one leg having a sharp free end directed outwardly for engaging said inside surface of said barrel.

2. The syringe assembly of claim 1, wherein said locking element is positioned with said sharp-free end contacting said interior surface of said plunger rod proximally of said at least one detent in said plunger rod, said post is positioned in said aperture of said locking element and said at least one finger element is contacting the proximal most of said at least two post detents, so that applying a proximally directed force to said plunger rod while holding said barrel causes said plunger rod to move proximally with respect to said stopper until said free end of said cantilevered leg moves distally along said inner surface of said plunger rod cavity to said at least one detent in said cavity and at least one motion limiting discontinuity on said secondary post causes said stopper to move along with said plunger in a proximal direction for a selected distance, and subsequently applying a distally directed force to said plunger rod to discharge fluid from said chamber through said passageway causes said plunger rod to move in a distal direction along with said locking element due to its engagement with said at least two post detents until said at least one motion limiting discontinuity on said secondary post causes said stopper to move distally with said plunger rod to discharge fluid from said chamber, after which applying proximally directed force to said plunger rod will cause said plunger rod to move proximally with said free end of said cantilevered leg moving distally along said interior surface of said cavity past said distal end of said plunger rod so that said at least one cantilevered leg engages said inside surface of said barrel to help prevent proximal movement of said stopper to render said syringe assembly unusable.

3. The syringe assembly of claim 2 further including a frangible zone on said stopper positioned distally from said discontinuity on said secondary post for allowing the plunger rod to disconnect from said stopper sealing element during application of excessive proximally-directed force to said plunger rod in an attempt to overcome said locking element's engagement of said inside surface of said barrel.

4. The syringe assembly of claim 3 wherein said frangible zone includes a zone of reduced cross-sectional area weaker than said post and said secondary post in areas outside said zone.

5. The syringe assembly of claim 3 wherein said frangible zone is located within said cavity of said plunger rod.

6. The syringe assembly of claim 2 having a discontinuity on said inside surface of said barrel side wall positioned to engage said sharp free end of said locking element when said sharp free end is contacting said inside surface of said barrel.

7. The syringe assembly of claim 2 wherein said distal wall of said barrel further includes an elongate tip extending distally therefrom having a passageway in fluid communication with said passageway in said distal wall.

8. The syringe assembly of claim 1 wherein said at least one detent in said plunger rod includes two axially spaced detents and said at least two detents on said post includes three axially spaced post detents so that said plunger rod can be moved distally two times before proximal motion of said plunger rod causes said locking element to engage said inside surface of said barrel.

9. The syringe assembly of claim 8 said at least one cantilevered leg of said locking element includes two cantilevered legs positioned on opposite sides of said central body portion.

10. The syringe assembly of claim 9 further including two radial projections on said stopper positioned to engage and force said two cantilevered legs outwardly when excessive proximally directed force is applied to said plunger rod in an attempt to overcome said locking element's engagement of said inside surface of said barrel.

11. The syringe assembly of claim 8 wherein said two axially spaced detents in said plunger rod include two axially spaced steps each having a blunt surface at its distal end extending inwardly from said interior surface.

12. The syringe assembly of claim 8 wherein said three axially spaced post detents each include a blunt distally facing surface at a extending radially outwardly.

13. The syringe assembly of claim 1 wherein said at least one motion limiting discontinuity on said secondary post comprises an outwardly directed projection and said at least one discontinuity in said secondary cavity comprises an inwardly directed projection.

14. The syringe assembly of claim 1 further including a needle cannula having a distal end, a proximal end and a lumen therethrough, said proximal end of said needle cannula being connected to said distal end of said barrel so that said lumen is in fluid communication with said passageway.

15. The syringe assembly of claim 1 wherein said locking element is made of sheet metal.

16. The syringe assembly of claim 1 wherein said stopper is integrally formed of thermoplastic material.

17. An operable syringe assembly having passive disabling structure comprising:
a barrel including a cylindrical side wall having an inside surface defining a chamber for retaining fluid,
an open proximal end and a distal end including a distal wall having a passageway therethrough in fluid communication with said chamber;
an elongate hollow plunger rod having a proximal end, an open distal end and an interior surface defining a cavity;
a stopper including a circular-shaped sealing element having a peripheral surface forming a seal with said inside surface of said barrel and a post projecting proximally from said sealing element;
a locking element including a central body portion having at least one cantilevered leg extending distally outwardly from said body portion, said at least one leg having a sharp free end directed outwardly for engaging said inside surface of said barrel, said locking element being movably engaged to said post and movably engaged to said plunger rod interior surface;
wherein, said locking element is indexed distally in said plunger rod during proximal motion of said plunger rod to draw fluid into said chamber and said locking element is indexed distally on said post of said stopper during distally directed motion of said plunger rod for delivering fluid from said chamber through said passageway, free axial movement of said stopper is limited with respect to said plunger rod to allow locking element to be indexed and for applying proximally and distally directed forces to said stopper through said plunger rod.

18. The syringe assembly of claim 17 further including:
at least one detent on said interior surface of said plunger rod and a secondary cavity proximal to said cavity having a discontinuity therein;
at least two post detents on said post and a secondary post projecting proximally from said post and having a discontinuity thereon; and
said locking element including at least one finger element extending inwardly from an aperture in said central body portion, said locking element being positioned with said sharp free end contacting said interior surface of said plunger rod proximally of said at least one detent, said post being positioned in said aperture of said locking element wherein said at least one finger element is contacting the proximal most of said at least two post detents and said secondary post being positioned in said secondary cavity so that said secondary post detent is proximal with respect to said secondary cavity detent and capable of engaging said secondary cavity discontinuity.

19. The syringe assembly of claim 18 wherein said three axially spaced post detents each include a blunt distally facing surface at a distal end of each of said detents.

20. The syringe assembly of claim 19 further including two radial cam projections on said stopper positioned to contact and force said two cantilevered legs outwardly when excessive proximally directed force is applied to said plunger rod in an attempt to overcome said locking element's engagement to said inside surface of said barrel.

21. The syringe assembly of claim 18 wherein said at least one detent in said plunger rod includes two axially spaced detents and said at least two detents on said post includes three axially spaced post detents so that said plunger rod can be moved distally two times before proximal motion of said plunger rod causes said locking element to engage said inside surface of said barrel.

22. The syringe assembly of claim 21 wherein said two axially spaced detents in said plunger rod include two axially spaced steps each having a blunt surface at its distal end extending inwardly from said interior surface.

23. The syringe assembly of claim 18 said at least one cantilevered leg of said locking element includes two cantilevered legs positioned on opposite sides of said central body portion and said at least one detent in said interior surface of said distal end of said plunger rod includes two detents positioned on opposite side of said plunger rod.

24. The syringe assembly of claim 17 having a discontinuity on said inside surface of said barrel side wall positioned to engage said sharp free end of said locking element when said sharp free end is contacting said inside surface of said barrel.

25. The syringe assembly of claim 17 wherein said distal wall of said barrel further includes an elongate tip extending distally therefrom having a passageway in fluid communication with said passageway in said distal wall.

26. The syringe assembly of claim 17 further including a needle cannula having a distal end, a proximal end and a lumen therethrough, said proximal end of said needle cannula being connected to said distal end of said barrel so that said lumen is in fluid communication with said passageway.

27. The syringe assembly of claim 17 wherein said locking element is made of sheet metal.

28. The syringe assembly of claim 17 wherein said stopper is integrally formed of thermoplastic material.

29. An operable syringe assembly having passive disabling structure comprising:
- a barrel including a side wall having an inside surface defining a chamber for retaining fluid, an open proximal end and a distal end including a distal wall having an elongate tip extending therefrom and a passageway therethrough in fluid communication with said chamber;
- an elongate plunger rod including a proximal end and an open distal end having an interior surface defining a cavity therein, two detents on said interior surface of said plunger rod, a secondary cavity at a proximal end of said cavity, said secondary cavity having a distal end and a proximal end, said secondary cavity having a contact surface at its proximal end and at least one discontinuity therein;
- a stopper including a circularly-shaped sealing element having a peripheral surface forming a seal with said inside surface of said barrel, a post extending proximally from said sealing element having a proximal end and a distal end, three axially-spaced post detents on said post, a secondary post extending axially from said proximal end of said post, having a proximal end and a distal end and at least one discontinuity on its surface, said secondary post being positioned at least partially in said secondary cavity, said stopper being free to move axially with respect to said plunger rod for a limited distance, said limited distance being determined by said secondary post contacting said contact surface and said secondary post discontinuity contacting said secondary cavity discontinuity;
- a locking element including a central body portion having an aperture therethrough, two cantilevered legs extending distally outwardly opposite sides of said body portion, and at least one finger element extending proximally inwardly into said aperture, each of said legs having a sharp-free end directed outwardly for engaging said inside surface of said barrel;
- said locking element being positioned with said sharp-free ends contacting said interior surface of said plunger rod proximally of said two detents in said plunger rod, said post being positioned in said aperture of said locking element wherein said at least one finger element is contacting said proximal-most of said three post detents, so that applying a proximally directed force to said plunger rod while holding said barrel causes said plunger rod to move proximally with respect to said stopper until said free end of said cantilevered legs move distally along said inner surface of said plunger rod cavity to the proximal-most of said two axially-spaced detents in said cavity and said secondary post discontinuity engages said secondary cavity discontinuity to move said stopper in a proximal direction along with the plunger rod for a selected distance, and subsequently applying a distally directed force to said plunger rod to discharge fluid from said chamber through said passageway causes said plunger rod to move in a distal direction along with said locking element due to said locking element's engagement with the proximal-most of said post detents until said secondary post contacts said contact surface of said secondary cavity to move said stopper distally to discharge fluid from said chamber,
- an additional proximal and distal motion of said plunger rod to draw fluid into said chamber and to deliver fluid from said chamber will cause said locking element to be repositioned so that said cantilevered legs are positioned to engage the distal-most of said two plunger rod detents and said at least one finger element is positioned in the distal-most of said three post detents,
- after which applying proximally directed force to said plunger rod will cause said plunger rod to move proximally with said free end of said cantilevered leg moving distally along said interior surface of said cavity past said distal end of said plunger rod so that said two cantilevered legs engage said inside surface of said barrel to help prevent proximal movement of said stopper to render said syringe assembly unusable.

* * * * *